United States Patent
Jawale et al.

(10) Patent No.: US 12,415,064 B2
(45) Date of Patent: Sep. 16, 2025

(54) ADJUSTABLE PRESSURE REGULATING AND PRESSURE INDICATING NEEDLE-FREE CONNECTORS

(71) Applicant: CareFusion 303, Inc., San Diego, CA (US)

(72) Inventors: Ankita Jawale, Nashik (IN); Abin Austin, Thrissur (IN); Amarsinh Deeliprao Jadhav, Bangalore (IN); Kanjimpuredathil Muralikrishna Menon, Bangalore (IN)

(73) Assignee: CAREFUSION 303, INC., San Diego, CA (US)

( * ) Notice: Subject to any disclaimer, the term of this patent is extended or adjusted under 35 U.S.C. 154(b) by 659 days.

(21) Appl. No.: 17/867,266

(22) Filed: Jul. 18, 2022

(65) Prior Publication Data

US 2023/0078397 A1 Mar. 16, 2023

Related U.S. Application Data

(60) Provisional application No. 63/301,616, filed on Jan. 21, 2022, provisional application No. 63/243,413, filed on Sep. 13, 2021.

(51) Int. Cl.
*A61M 39/24* (2006.01)
*A61M 39/10* (2006.01)

(52) U.S. Cl.
CPC ............ *A61M 39/24* (2013.01); *A61M 39/10* (2013.01); *A61M 2205/0216* (2013.01); *A61M 2205/3331* (2013.01)

(58) Field of Classification Search
CPC .................. A61M 39/24; A61M 39/10; A61M 2205/0216; A61M 2205/3331;
(Continued)

(56) References Cited

U.S. PATENT DOCUMENTS

| 4,863,429 A | 9/1989 | Baldwin |
| 5,322,511 A | 6/1994 | Armbruster et al. |

(Continued)

FOREIGN PATENT DOCUMENTS

| CA | 2906335 A1 * | 9/2014 | .......... A61M 39/223 |
| WO | WO-2006062912 A1 * | 6/2006 | ............ A61M 39/26 |

OTHER PUBLICATIONS

Queensland Department of Health, "Peripheral intravenous catheter (PIVC) Guideline", Queensland Health, 2012, retrieved from the internet at https://www.health.qld.gov.au/_data/assets/pdf_file/0025/444490/icare-pivc-guideline.pdf.

(Continued)

*Primary Examiner* — Cris L. Rodriguez
(74) *Attorney, Agent, or Firm* — MASCHOFF BRENNAN

(57) ABSTRACT

A needle-free connector assembly is provided that includes a main housing coupled to an indicator housing. A plunger is coupled to a bellows disposed in the main housing. An inlet port is disposed at an upstream end of the indicator housing and an outlet port is disposed at a downstream end of the main housing, with a valve disposed within the indicator housing and adjacent the inlet port. A switch member is slidingly disposed in the main housing, wherein the needle-free connector assembly provides both flow regulation and pressure indication when the switch member is in a downstream position and only pressure indication when the switch member is in an upstream position. Infusion sets and methods of operating a needle-free connector are also provided.

17 Claims, 18 Drawing Sheets

(58) Field of Classification Search
CPC ............... A61M 5/482; A61M 5/488; A61M 2039/2413; A61M 2039/242; A61M 5/486; A61M 2039/2486
See application file for complete search history.

(56) References Cited

U.S. PATENT DOCUMENTS

| | | | | |
|---|---|---|---|---|
| 6,113,068 | A * | 9/2000 | Ryan | A61M 39/045 604/905 |
| 6,945,954 | B2 | 9/2005 | Hochman et al. | |
| 7,766,304 | B2 * | 8/2010 | Phillips | A61M 39/26 604/905 |
| 7,766,897 | B2 * | 8/2010 | Ramsey | A61M 39/20 604/533 |
| 7,993,328 | B2 * | 8/2011 | Whitley | A61M 39/26 604/537 |
| 8,137,303 | B2 * | 3/2012 | Stout | G09F 3/0291 604/361 |
| 8,182,452 | B2 * | 5/2012 | Mansour | A61M 39/10 604/536 |
| 8,251,346 | B2 * | 8/2012 | Stroup | A61M 5/16881 251/149.6 |
| 8,298,196 | B1 | 10/2012 | Mansour | |
| 8,603,047 | B2 * | 12/2013 | Stroup | A61M 39/10 604/207 |
| 8,888,758 | B2 * | 11/2014 | Mansour | A61M 39/22 604/533 |
| 9,308,362 | B2 * | 4/2016 | Mansour | A61M 39/26 |
| 9,849,277 | B2 * | 12/2017 | Stroup | A61M 39/22 |
| 10,269,266 | B2 | 4/2019 | Rios et al. | |
| 10,299,993 | B2 * | 5/2019 | Stroup | A61M 5/14228 |
| 11,253,689 | B2 * | 2/2022 | Mansour | A61M 39/10 |
| 11,389,635 | B2 * | 7/2022 | Mason | A61M 39/162 |
| 12,337,161 | B2 * | 6/2025 | Jadhav | A61M 39/24 |
| 2005/0049556 | A1 | 3/2005 | Tanaka | |
| 2005/0087715 | A1 * | 4/2005 | Doyle | A61M 39/26 604/537 |
| 2006/0118749 | A1 * | 6/2006 | Ryan | A61M 39/26 251/149.7 |
| 2009/0145349 | A1 | 6/2009 | Hebert | |
| 2014/0194851 | A1 | 7/2014 | Burke et al. | |
| 2015/0065956 | A1 | 3/2015 | Huang et al. | |
| 2016/0106916 | A1 | 4/2016 | Burmaster | |
| 2019/0336707 | A1 | 11/2019 | Yu et al. | |
| 2022/0313904 | A1 * | 10/2022 | Jadhav | A61M 39/24 |
| 2023/0057569 | A1 * | 2/2023 | Jadhav | A61M 25/0097 |
| 2025/0065098 | A1 * | 2/2025 | Yeh | A61M 39/00 |

OTHER PUBLICATIONS

International Search Report and Written Opinion in Application No. PCT/US2022/039841, dated Nov. 2, 2022, 14 pages.

* cited by examiner

3ml Syringe

| # | Force on Plunger (lbf) | Pressure Generated (psi) |
|---|---|---|
| 1 | 1 | 11.14 |
| 2 | 1 | 22.3 |
| 3 | 2.25 | 25.08 |
| 4 | 3 | 33.43 |

5ml Syringe

| # | Force on Plunger (lbf) | Pressure Generated (psi) |
|---|---|---|
| 1 | 1 | 5.84 |
| 2 | 2 | 11.68 |
| 3 | 3 | 17.51 |
| 4 | 4 | 23.35 |
| 5 | 4.3 | 25.1 |

10ml Syringe

| # | Force on Plunger (lbf) | Pressure Generated (psi) |
|---|---|---|
| 1 | 1 | 4.05 |
| 2 | 2 | 8.09 |
| 3 | 3 | 14.14 |
| 4 | 4 | 16.18 |
| 5 | 5 | 20.23 |
| 6 | 6 | 24.27 |
| 7 | 6.2 | 25.08 |

FIG. 29

ADJUSTABLE PRESSURE REGULATING AND PRESSURE INDICATING NEEDLE-FREE CONNECTORS

CROSS-REFERENCE TO RELATED APPLICATIONS

This application claims the benefit of priority under 35 U.S.C. § 119 to U.S. Provisional Patent Application Ser. No. 63/301,616, entitled "ADJUSTABLE PRESSURE REGULATING AND PRESSURE INDICATING NEEDLE-FREE CONNECTOR," filed on Jan. 21, 2022, and U.S. Provisional Patent Application Ser. No. 63/243,413, entitled "PRESSURE INDICATING NEEDLE-FREE CONNECTOR," filed on Sep. 13, 2021, 2021, the entire contents of which are incorporated herein by reference.

TECHNICAL FIELD

The present disclosure generally relates to infusion set intravenous (IV) connectors, in particular adjustable pressure regulating and/or pressure indicating needle-free connectors.

BACKGROUND

Typical infusion or intravenous (IV) sets are constructed by joining polymeric tubing segments to polymeric components, many of which use needle-free connectors. These IV sets can be used with infusion pumps or gravity systems to provide fluids via a catheter to a user, such as a patient. Typical needle-free connectors do not provide an indication of the infusion pressure of the fluid administered through the connector. However, pressure regulation is needed to provide infusion therapy for specific conditions such as for chemotherapy, infusion in neonates, infusion in geriatric patients, power injection, etc.

For instance, the pressure applied to the blood component should not exceed 300 mm Hg (5 psi) as this may result in hemolysis or bag breakage. As another example, during power injection, the IV fluid needs to be injected in bolus without control. As yet another example, United States Department of Health guidelines indicate that the infusion pressure should not exceed 25 pounds per square inch (psi), as infusion pressures higher than 25 psi may damage blood vessels and negatively affect patient health and comfort.

For these reasons, it is desirable to provide needle-free connectors for use with IV components and IV sets that provide adjustable infusion pressure regulation and/or pressure indication for fluid being delivered through the connector to avoid exceeding critical delivery pressure thresholds.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 29 depicts generated pressure tables for various sizes of syringes, according to aspects of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
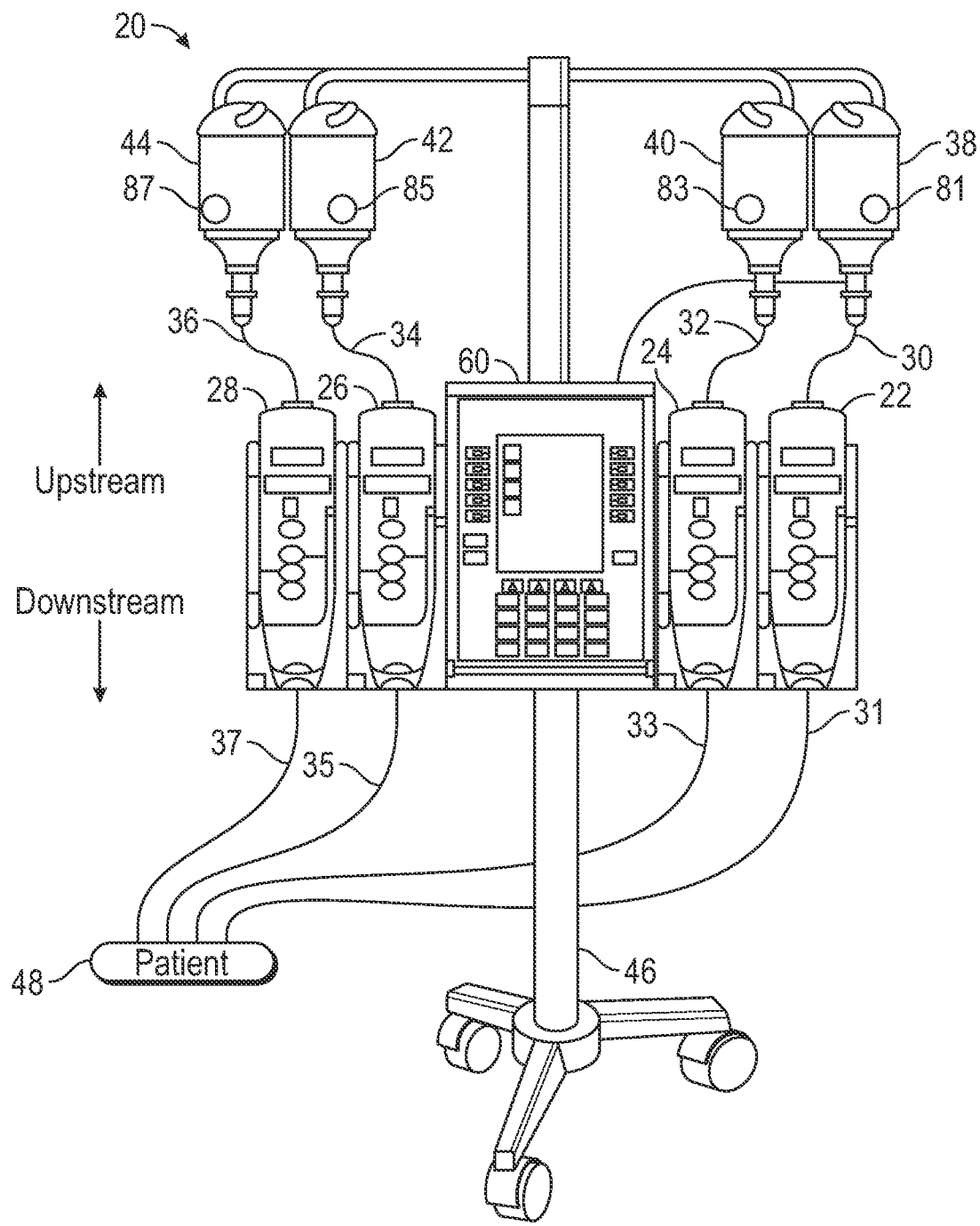
FIG. 1 depicts a perspective view of an example patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids. The infusion pumps 22, 24, 26, and 28 are controlled by a pump control unit 60.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typical infusion sets may also be gravity sets that do not require use of an infusion pump. For example, any of fluid supplies 38, 40, 42, and 44 may be directly connected to the patient 48 via a gravity IV set, wherein gravity causes the fluid to flow through the infusion set and into the patient 48 without the aid of a pump.

Figure 2:
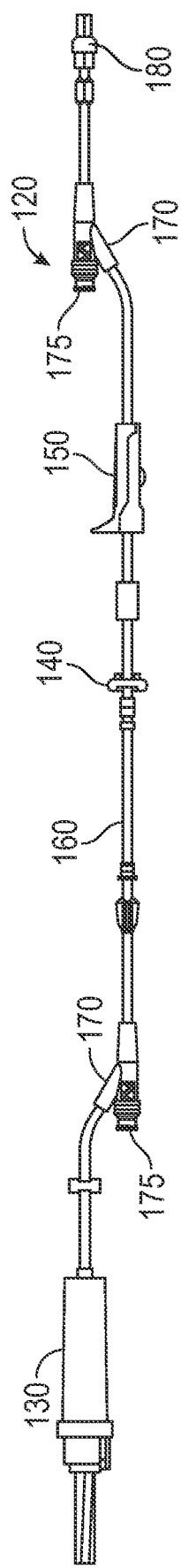
FIG. 2 depicts a top view of a typical assembled IV infusion set.

Typically, medical fluid administration sets have more parts than are shown in FIG. 1, such as those shown in FIG. 2. Infusion sets may be formed from any combination of infusion components and tubing. Typically, the infusion components and tubing are disposable products that are used once and then discarded. The infusion components and tubing may be formed from any suitable material (e.g., plastic, silicone, rubber), many or all of which are clear or translucent so that the fluid flow or levels inside can be seen.

As shown in FIG. 2, an infusion set 120 may include a drip chamber 130, a check valve 140 and a roller clamp 150 connected together by tubing 160. The infusion set 120 may also include a Y-site 170 having a Y-shaped junction with a needle-free connector 175, as well as a luer lock connector 180 at the end of the infusion set 120. The luer lock connector 180 may be used for connection to a catheter inserted into a patient, for example. The infusion set 120 may include additional infusion components and may be formed of any combination of components and the tubing 160.

Figure 3:
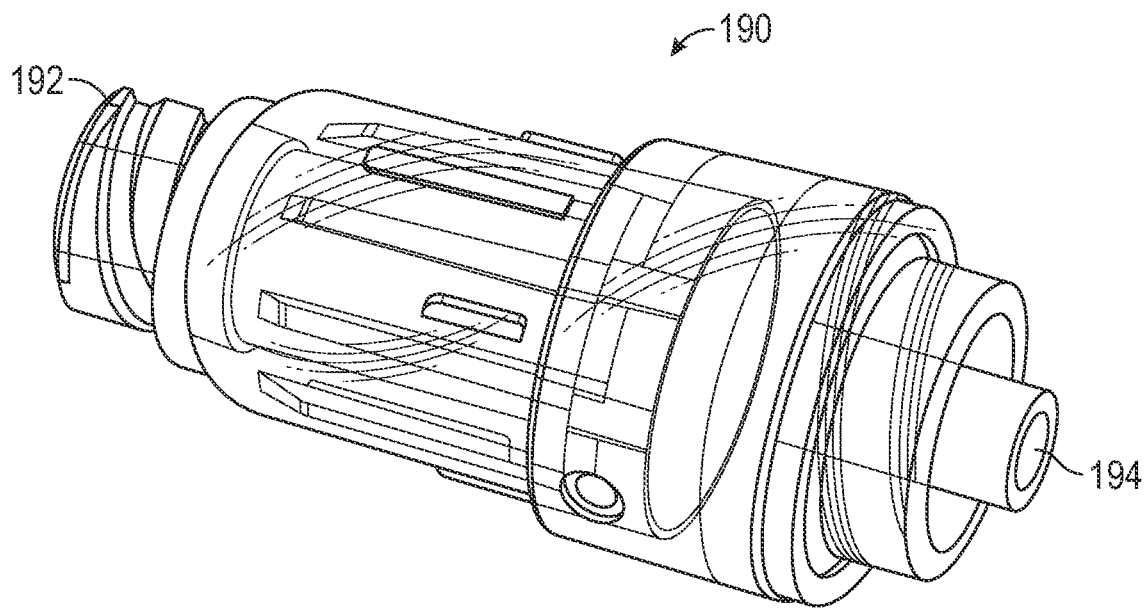
FIG. 3 depicts a perspective view of a typical needle-free connector.
Figure 4:
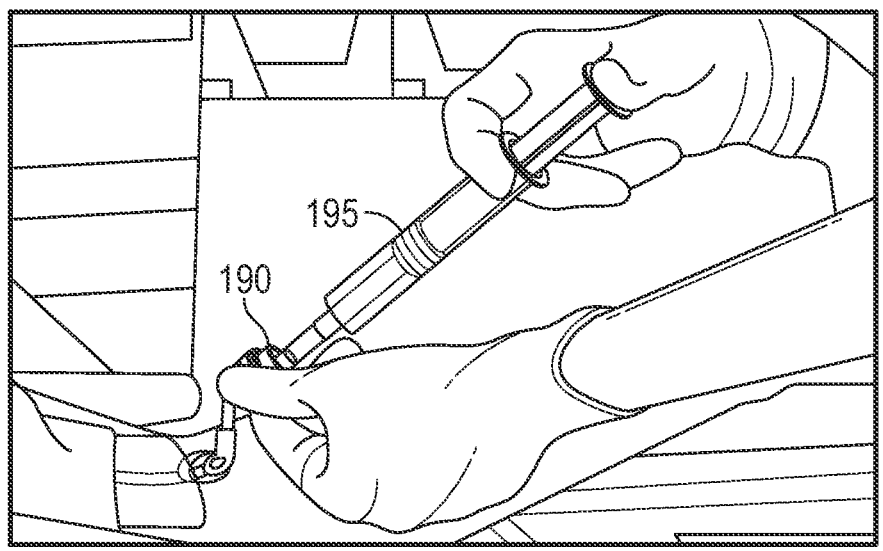
FIG. 4 depicts a perspective view of the needle-free connector of FIG. 3 in use.
Figure 5:
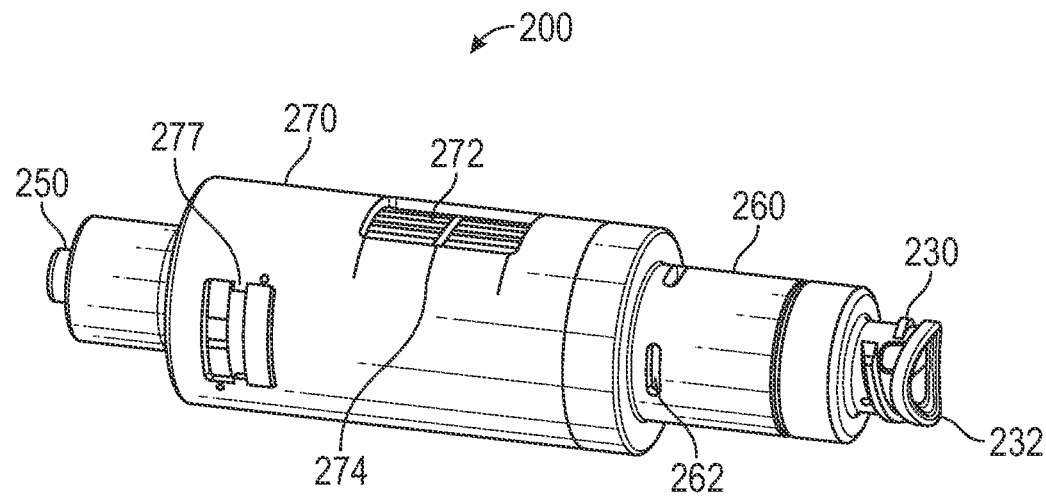
FIG. 5 depicts a perspective view of an adjustable needle-free connector assembly, according to aspects of the disclosure.

As shown in FIGS. 3 and 4, a typical needle-free connector 190 may be used to provide a connection point for a needle-free syringe 195. The needle-free connector 190 has a inlet port 192 and an outlet port 194. As seen in FIG. 4, a needle-free syringe 195 may be connected to the inlet port 192 of the needle-free connector 190 in order to deliver fluid from the needle-free syringe 195 into a catheter line connected to the outlet port 194 of the needle-free connector 190.

Needle-free connectors are essential devices to deliver fluid to a patient via an IV catheter. Needle-free connectors may be used in general patient populations, including neonatal, pediatric and adult patients. In various applications, the pressure applied to the blood component should not exceed 300 mm Hg (5 psi) as this may result in hemolysis or bag breakage, the IV fluid needs to be injected in bolus without control during power injection and infusion pressure should never exceed 25 psi, as pressure higher than 25 psi may damage blood vessels. Thus, clinicians face challenges to maintain the various higher-pressure limits during infusion delivery with typical connectors.

As shown in FIGS. 5 through 21, an adjustable needle-free connector assembly 200 is provided according to aspects of the disclosure. Needle-free connector 200 has a plunger 210 coupled to an elastomeric bellows 220, as well as an inlet port 230, a sealing member 232, a valve 240 and an outlet port 250, with the inlet port 230 being an upstream end and the outlet port 250 being a downstream end. A plunger tip 212 and the valve 240 are disposed within an indicator housing 260, where the plunger tip 212 includes one or more flow openings 214 that fluidly couple the exterior of the plunger tip 212 with a lumen 216 defining a fluid flow path within the plunger 210. The flow openings 214 (e.g., circular hole, oval hole) allow fluid to flow through from the inlet port 230, through the plunger tip 212 and into the lumen 216, which in turn flows out of the outlet port 250.

The indicator housing 260 includes one or more pressure viewing windows 262, such as four pressure viewing windows 262 circumferentially spaced around the indicator housing 260, for example, though any suitable number of pressure viewing windows 262 may be provided. The valve 240 may include multiple indicator bands 242 disposed on an outer surface of the valve 240 (e.g., circumferential bands). The indicator bands 242 may have visual differences (e.g., colors, shadings, textures, written words). For example, an upstream indicator band 242a may be red to indicate the fluid pressure is higher than the desired threshold (e.g., 25 psi and a downstream indicator band 242b may be green to indicate the fluid pressure is in the ideal range (e.g., just below 25 psi). In aspects of the disclosure, any number of indicator bands 242 may be present to indicate different levels of pressure (e.g., a yellow indicator band downstream of the green indicator band 242b to indicate little or no pressure).

The indicator band 242 that corresponds to the current pressure condition may be aligned with the pressure viewing windows 262, thus providing visual indication to a user (e.g., clinician) of the pressure status within the needle-free connector 200. For example, in the above-described example of four pressure viewing windows 262, when the red indicator band 242a is aligned, a user can see the red indicator through any of the four pressure viewing windows 262, thus providing a visual indicator of excessive fluid pressure to the user from any line of sight around the indicator housing 260.

The valve 240 may include one or more valve openings 244 coupled with one or more valve channels 246 that are fluidly coupled to the inlet port 230. The valve openings 244 are disposed in an inner wall 247 defining a valve bore 248. The plunger tip 212 is slidingly received within the valve bore 248. Thus, when the plunger tip 212 is moved within the valve bore 248 such that the valve openings 244 are at least partially aligned with the flow openings 214 of the plunger tip 212, a fluid flow path is open from the valve channels 246, through the valve openings 244 and through the flow openings 214 into the lumen 216 of the plunger 210. Conversely, when the plunger tip 212 is moved within the valve bore 248 such that the flow openings 214 are adjacent the inner wall 247, the flow path from the valve channels 246 is blocked by the inner wall 247 and fluid is prevented from flowing into the flow openings 214 and through the lumen 216, resulting in no fluid flow out of the outlet port 250.

A main housing 270 may be coupled to the indicator housing 260, the main housing 270 having one or more adjustment windows 272. An adjustment member 280 is disposed within the main housing 270, the adjustment member 280 having threads 284 configured to engage with threads 264 of the indicator housing 260 that extend within the main housing 270. The adjustment member 280 may include an indicator band 282 (e.g., circumferential band) disposed on an outer surface of the adjustment member 280. The indicator band 282 is visible through the adjustment windows 272, thus providing a visual indication of the preload pressure setting.

Figure 8:
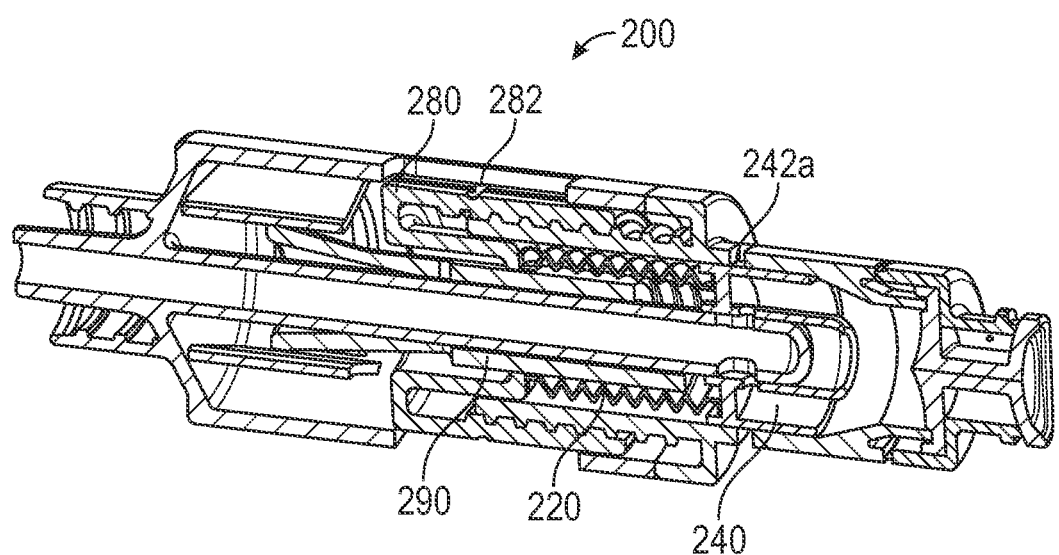
FIG. 8 depicts a cross-section perspective view of the needle-free connector assembly of FIG. 5 with regulation mode switched off, according to aspects of the disclosure.
Figure 9:
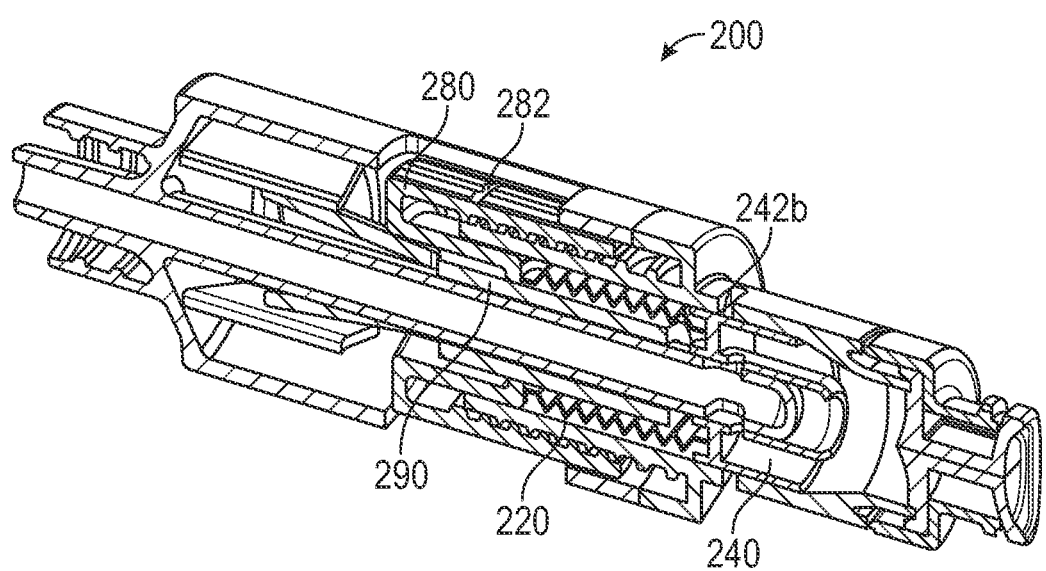
FIG. 9 depicts a cross-section perspective view of the needle-free connector assembly of FIG. 5 with a preload adjustment, according to aspects of the disclosure.

As shown in FIGS. 8 and 9, the needle-free connector assembly 200 may be preloaded by a thread adjustment (e.g., threaded engagement between threads 264, 284) to set the red pressure indication at a desired level (e.g., 5 psi when hemolysis or bag breakage is a concern or 25 psi when damage to blood vessels is a concern). For example, a user may reach through the adjustment windows 272 to rotate the adjustment member 280 to the desired load setting, such as from the adjustment member 280 position in FIG. 8 to the adjustment member 280 position in FIG. 9 In aspects of the disclosure, gradation markings 274 may be disposed on the main housing 270 adjacent the adjustment windows 272 (see FIG. 5). For example, the gradation markings 274 may be alignment marks and/or may include word marks (e.g., 5 psi, 15 psi, 25 psi) and/or design marks (e.g., diagrams).

The bellows 220 may be disposed within the indicator housing 260 (e.g., portion having threads 264) and between/ engaged by a downstream surface 241 of the valve 240 and a lip 286 of the adjustment member 280. The bellows 220 may be formed of a soft or pliable material that provides for repeated compression and expansion of the bellows 220. The material of the bellows 220 may be designed to provide a desired amount of biasing force to cause the bellows 220 to push in an opening or expanded direction. Thus, a specific amount of fluid flow pressure is required to overcome the biasing force and cause the bellows 220 to move in a closed or compressed direction. Also, the amount of thread adjustment/preload of the adjustment member 280 dictates the amount of compression of the bellows 220. For example, the further upstream the adjustment member 280 is threaded, the more compressed the bellows 220 will be.

Figure 6:
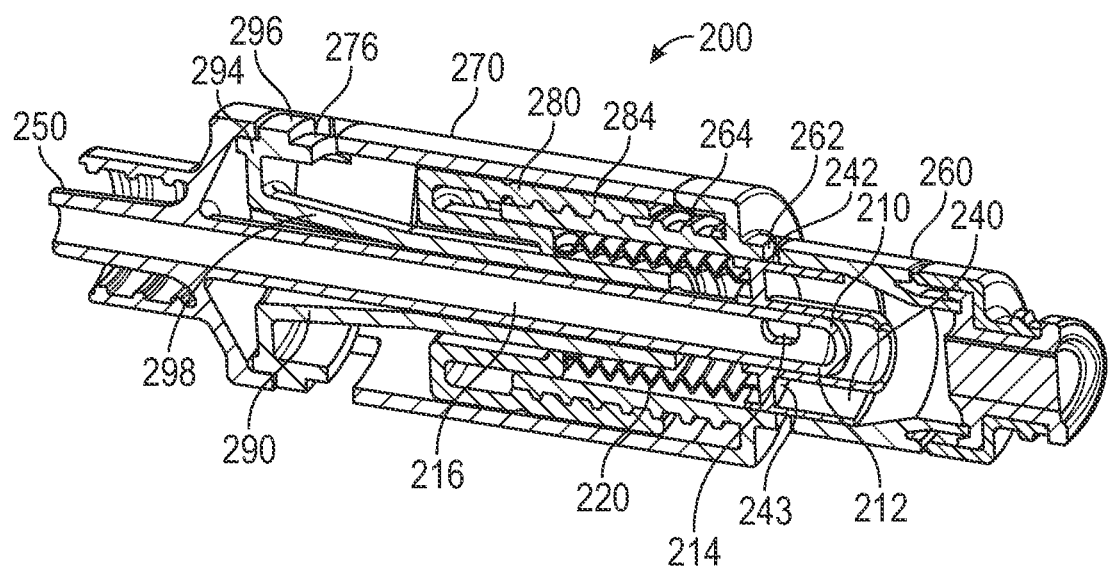
FIG. 6 depicts a cross-section perspective view of the needle-free connector assembly of FIG. 5 with regulation mode switched on, according to aspects of the disclosure.
Figure 7:
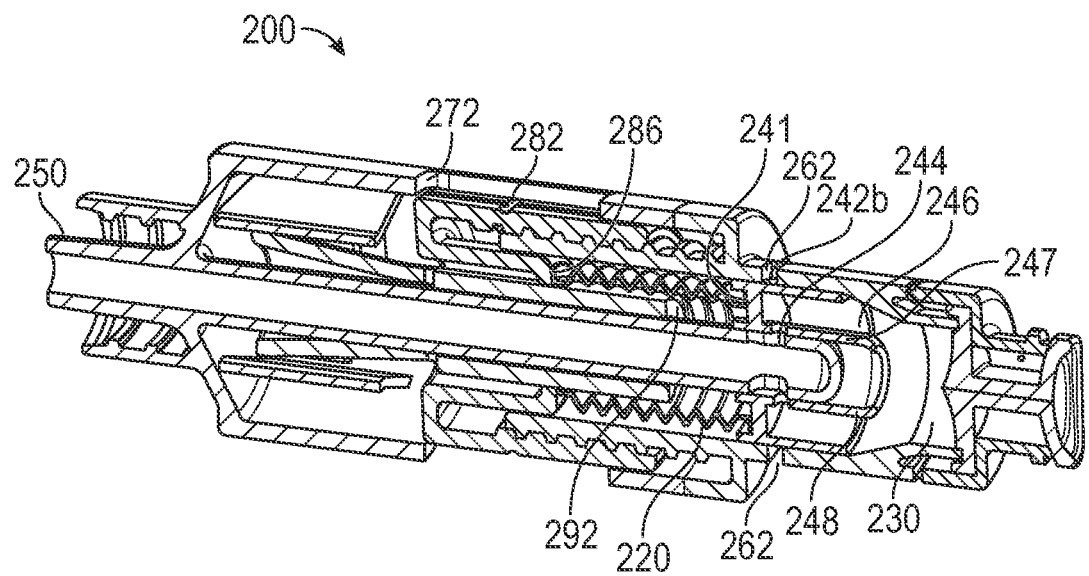
FIG. 7 depicts another cross-section perspective view of the needle-free connector assembly of FIG. 6, according to aspects of the disclosure.

As shown in FIGS. 6 and 7, a switch member 290 may be slidingly disposed within the main housing 270, the switch member 290 configured to turn flow regulation on or off. For example, if the switch member 290 is in a downstream position, the needle-free connector assembly 200 may provide both flow regulation and pressure indication functions. As another example, if the switch member 290 is in an upstream position, the needle-free connector assembly 200 may provide only the pressure indication function.

The switch member 290 may be slidingly disposed within the adjustment member 280 and the bellows 220, while the plunger 210 may be slidingly disposed within the switch member 290. For example, the plunger 210 may be a cylindrical structure that is sliding received within each of a cylindrical adjustment member 280, a cylindrical bellows 220 and a cylindrical valve 240, all of which are disposed within cylindrical main and indicator housings 270, 260, respectively. An upstream surface of the switch member may be a stop surface 292 configured to engage and prevent the downstream surface 241 of the valve 240 from moving further downstream within the indicator housing 260 when the switch member 290 is in the pressure indication only mode (e.g., regulation mode turned off).

The switch member 290 may include a protrusion 294 that is sliding disposed within a switch window 276 in the main housing 270. The switch window 276 may have one or more ribs 277 (see FIG. 5) that separate a regulation/pressure mode position of the protrusion 294 from a pressure only mode position of the protrusion 294. The switch member 290 may flare out at the location of the switch window 276) such that the switch member 290 is flexible at the downstream end 298. In use, the protrusion 294 may be pressed (e.g., pushed inward) through the switch window 276 and slid upstream or downstream of the ribs 277 to the desired position. An outer surface 296 of the protrusion 294 may be colored (e.g., red) to provide a visual indication of which position (e.g., regulation/indication mode, indication mode only) the switch member 290 is set to.

Figure 10:
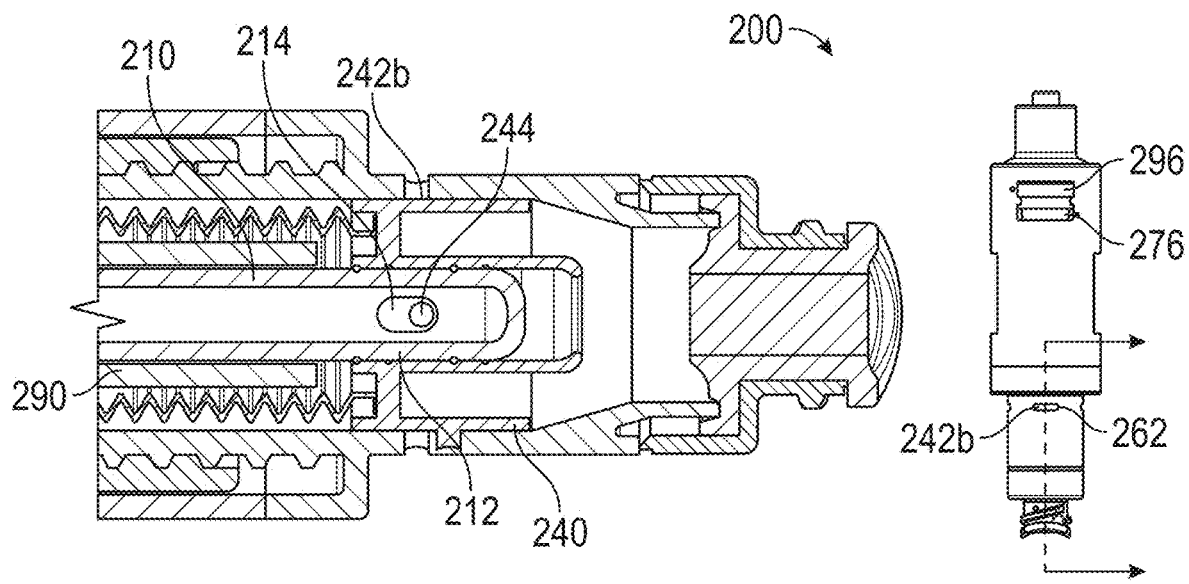
FIG. 10 depicts a cross-section partial front view of the needle-free connector assembly of FIG. 5 with plunger in home position and pressure regulation on, according to aspects of the disclosure.
Figure 11:
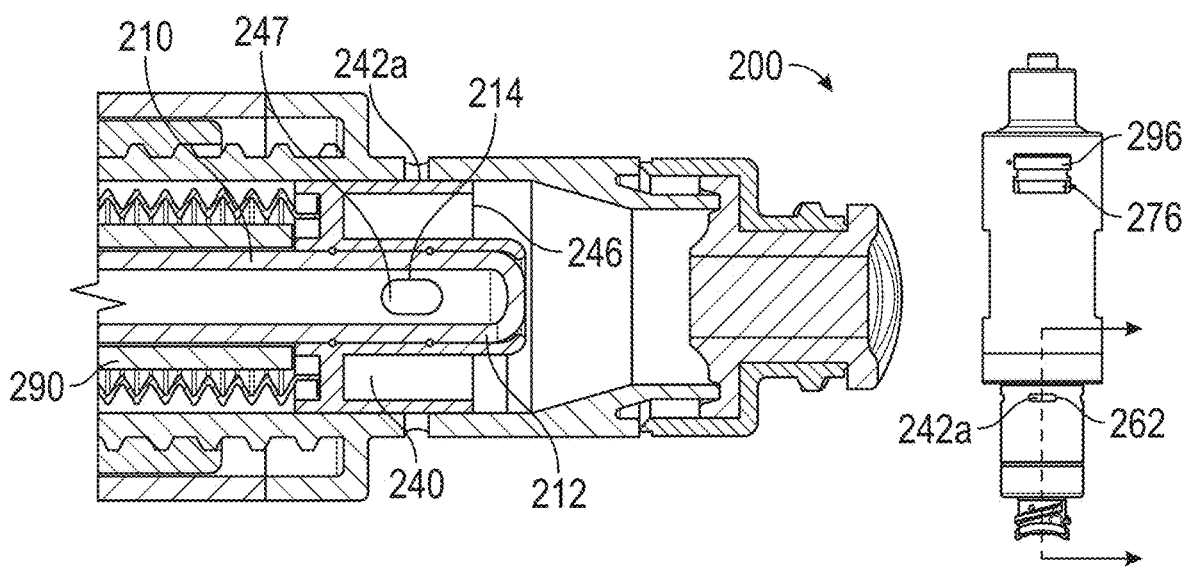
FIG. 11 depicts a cross-section partial front view of the needle-free connector assembly of FIG. 5 with plunger in regulation position and pressure regulation on, according to aspects of the disclosure.

As shown in FIGS. 10 and 11, when the switch member 290 is in the pressure regulation on position, the outer surface 296 is in the downstream position within the switch window 276 and the plunger 210 is in either a home position or a regulation position. For example, as shown in FIG. 10, the plunger 210 is in the home position such that the flow openings 214 of the plunger tip 212 align with the valve openings 244 of the valve 240 and the fluid flow pressure is less than or equal to the set pressure (e.g., desired pressure of 25 psi). Here, the green downstream indicator band 242b is visible through the viewing windows 262 of the indicator housing 260, providing a visual indication that the pressure is not exceeding the set level.

As shown in FIG. 11, the plunger 210 is in a regulation position such that the flow openings 214 of the plunger tip 212 do not align with the valve openings 244 of the valve 240, but instead align with the inner wall 247 so that fluid flow from the valve channels 246 is blocked. This occurs because the fluid flow pressure is greater than the set pressure (e.g., 25 psi) and the fluid pressure against a pressure pad 243 moves the valve 240 downstream as seen between FIGS. 10 and 11. Here, the red upstream indicator band 242a is visible through the viewing windows 262 of the indicator housing 260, providing a visual indication that the pressure has exceeded the set level. Thus, in the regulation mode, when the pressure exceeds the set level, the flow is automatically blocked by the movement of the valve 240.

Figure 12:
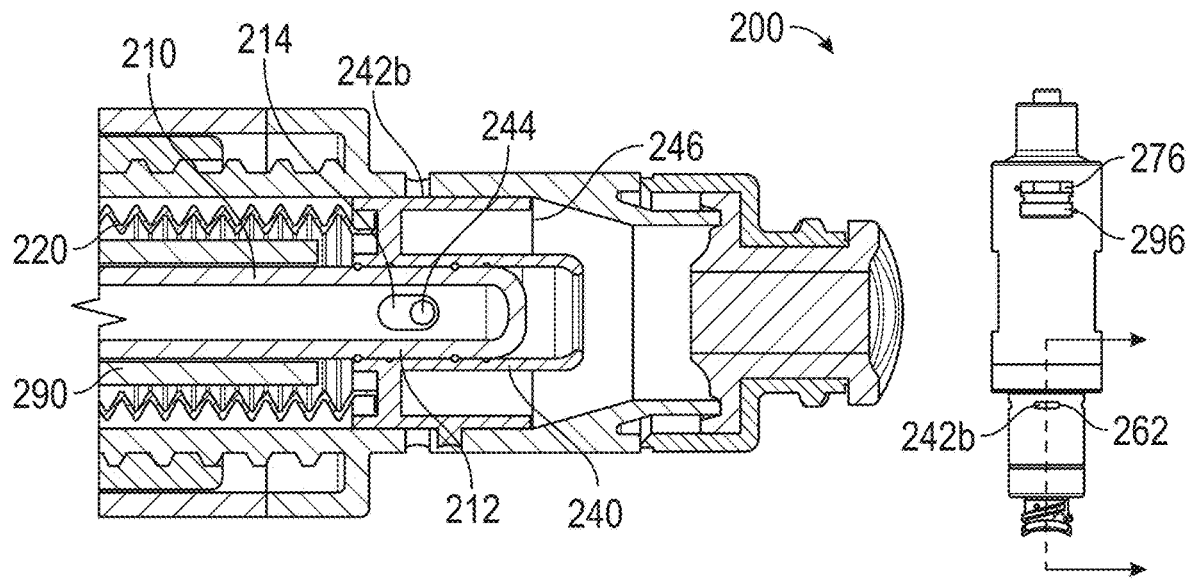
FIG. 12 depicts a cross-section partial front view of the needle-free connector assembly of FIG. 5 with plunger in home position and pressure regulation off, according to aspects of the disclosure.
Figure 13:
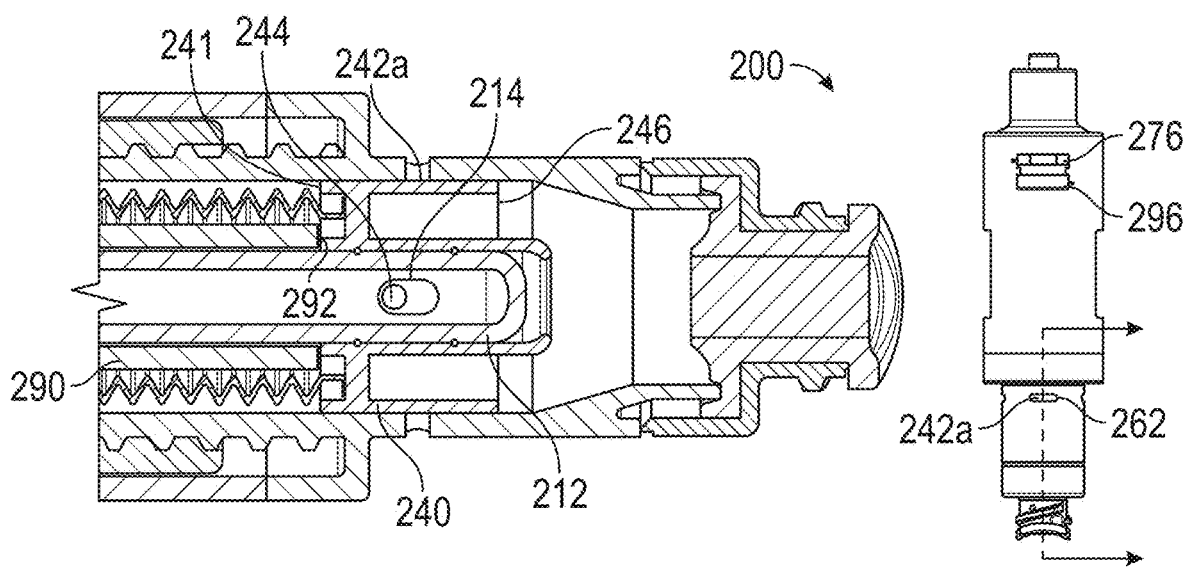
FIG. 13 depicts a cross-section partial front view of the needle-free connector assembly of FIG. 5 with plunger in regulation position and pressure regulation off, according to aspects of the disclosure.
Figure 14:
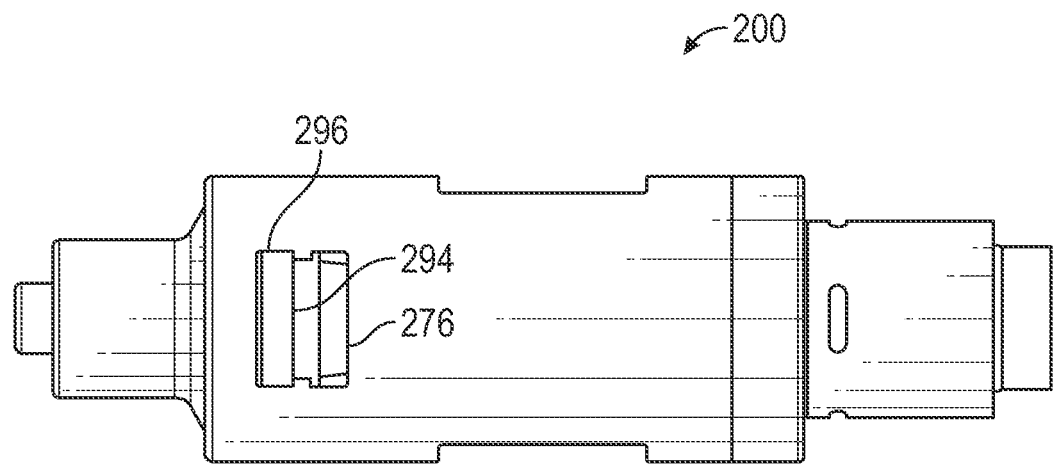
FIG. 14 depicts a front view of the needle-free connector assembly of FIG. 5 with regulation mode switched on, according to aspects of the disclosure.
Figure 15:
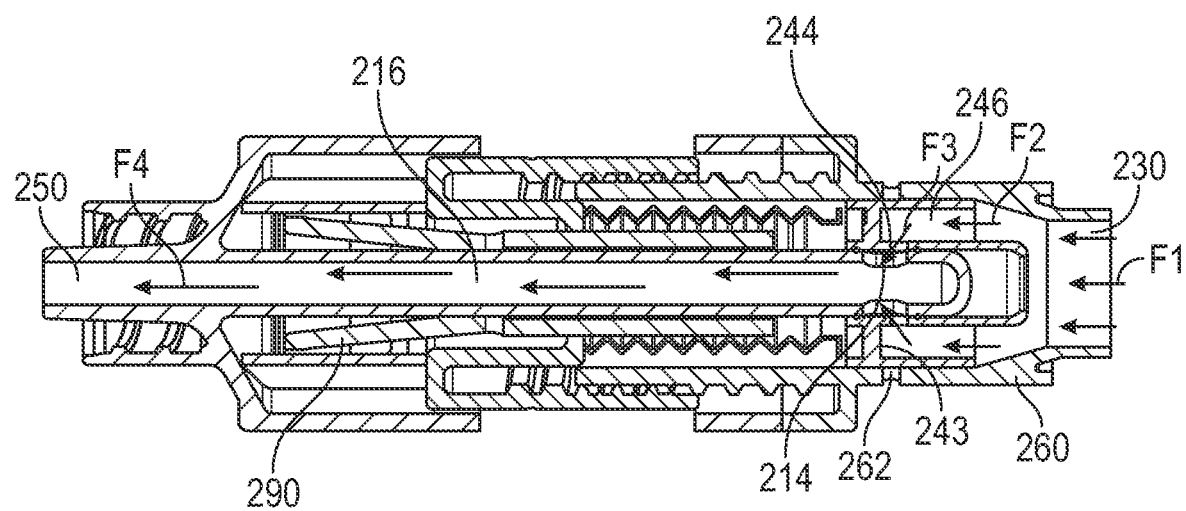
FIG. 15 depicts a cross-section front view of the needle-free connector assembly of FIG. 14 with full fluid flow, according to aspects of the disclosure.

As shown in FIGS. 12 and 13, when the switch member 290 is in the pressure regulation off position, the outer surface 296 is in the upstream position within the switch window 276 and the plunger 210 is in either a home position or a regulation position. For example, as shown in FIG. 12, the plunger 210 is in the home position such that an upstream portion of the flow openings 214 of the plunger tip 212 align with the valve openings 244 of the valve 240 and the fluid flow pressure is less than or equal to the set pressure (e.g., desired pressure of 25 psi). Here, the green downstream indicator band 242b is visible through the viewing windows 262 of the indicator housing 260, providing a visual indication that the pressure is not exceeding the set level.

As shown in FIG. 13, the plunger 210 is in a regulation position and downstream portions of the flow openings 214 of the plunger tip 212 align with the valve openings 244 of the valve 240 and the fluid flow pressure is greater than the set pressure. This greater fluid flow pressure of the fluid pressure against a pressure pad 243 moves the valve 240 downstream as seen between FIGS. 12 and 13, but still allows fluid flow as the valve openings 244 are still aligned with portions of the flow openings 214. Here, the red upstream indicator band 242a is visible through the viewing windows 262 of the indicator housing 260, providing a visual indication that the pressure has exceeded the set level. However, unlike in the regulation mode, in the indication only mode when the pressure exceeds the set level, the fluid flow continues despite the movement of the valve 240.

As can be seen in FIG. 13, when the switch member 290 is moved upstream when put in the indication only mode position, the stop surface 292 may engage the downstream surface 241 of the valve 240 and prevent further downstream movement of the valve 240, thus ensuring that the valve openings 244 are always aligned with some portion of the flow openings 214 and thus always providing for fluid flow through the needle-free connector assembly 200.

In use, when the needle-free connector assembly 200 is in the pressure regulation and pressure indication mode, as shown in FIGS. 14-17, the switch member 290 is set in the regulation/indication position (e.g., downstream position) as shown by the outer surface 296 of the protrusion 294 within the switch window 276. Here, the sealing member 232 is removed and a fluid source (e.g., needle-free syringe, IV tube) is connected to the inlet port 230. Thus, fluid flows into the inlet port 230 as indicated by fluid flow arrows F1, through the valve channels 246 as indicated by fluid flow arrows F2, through the valve openings 244/flow openings 214 as indicated by fluid flow arrows F3 and through the lumen 216 to the outlet port 250 as indicated by fluid flow arrows F4 (see FIGS. 15 and 16). Here, the pressure due to the fluid flow acts on the pressure pad 243 of the valve 240, causing the valve 240 to slide linearly within the indicator housing 260. As the valve 240 moves within the indicator housing 260, different indicator bands 242 may in turn be aligned with the viewing windows 262 of the indicator housing 260, thus providing a view of the color of that indicator band 242 through the viewing windows 262.

Figure 16:
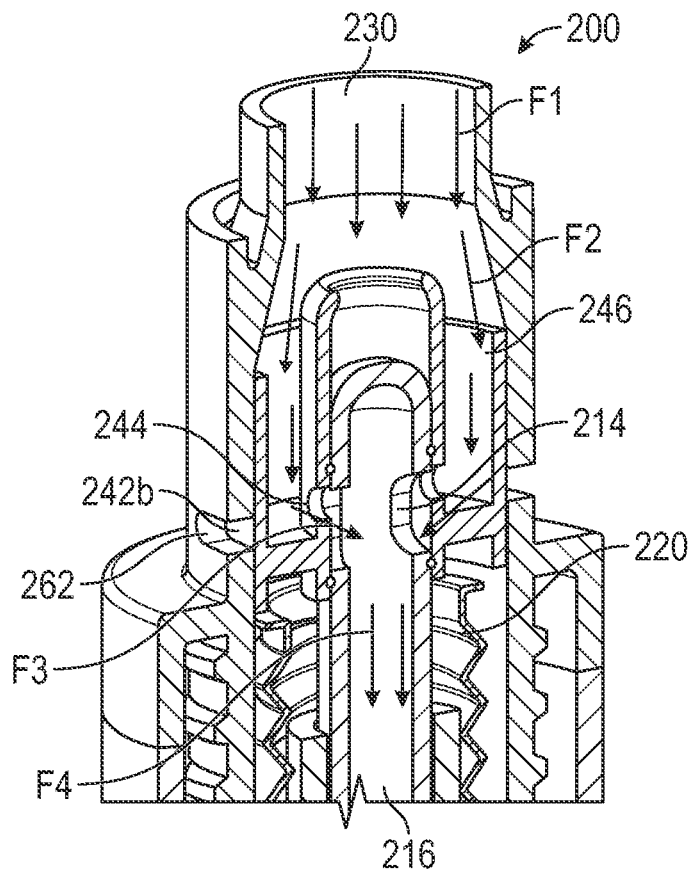
FIG. 16 depicts a cross-section partial perspective view of the needle-free connector assembly of FIG. 14 with fluid flow enabled, according to aspects of the disclosure.

For example, in desired fluid pressure state of the needle-free connector 200, the green indicator band 242b is aligned with the viewing windows 262 (as shown in FIG. 16) so that a user can easily and quickly see with a glance the green color in one or more of the viewing windows 262 and know that the fluid is currently flowing through the needle-free connector 200 at the desired pressure. As fluid is pushed into the needle-free connector 200 at higher pressure, such as by the user activating the needle-free syringe 195 shown in FIG. 4 or some other pressure inducing event, the bellows 220 compresses and the valve 240 slides downstream so that the red indicator band 242a is aligned with the viewing windows 262 (as shown in FIG. 17), again providing a quick visual indication to the user through one or more of the viewing windows 262 that the fluid pressure is exceeding a desirable pressure range (e.g., 24-25 psi).

Figure 17:
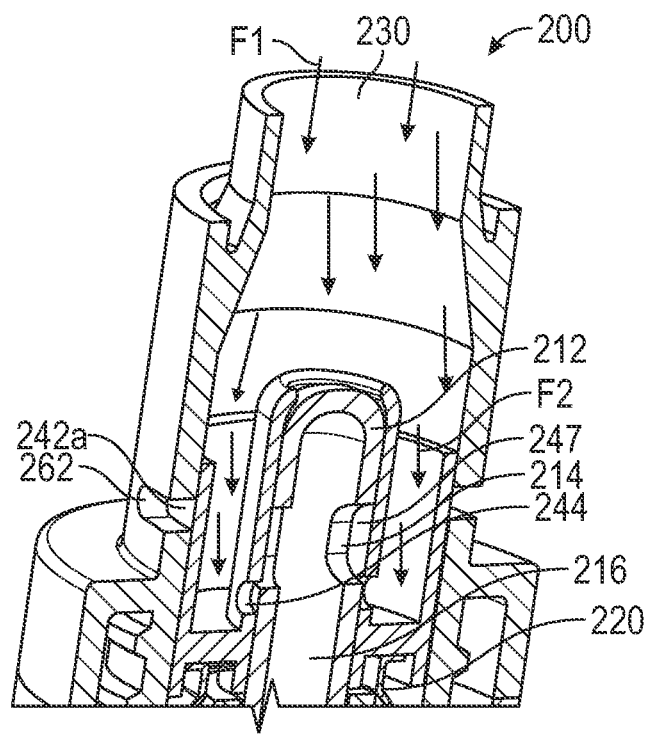
FIG. 17 depicts a cross-section partial perspective view of the needle-free connector assembly of FIG. 14 with fluid flow blocked, according to aspects of the disclosure.
Figure 18:
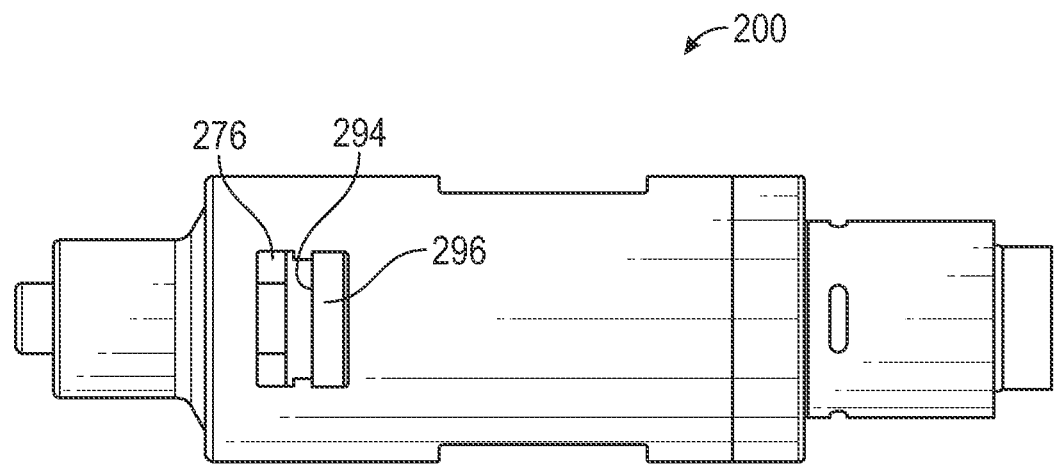
FIG. 18 depicts a front view of the needle-free connector assembly of FIG. 5 with regulation mode switched off, according to aspects of the disclosure.
Figure 19:
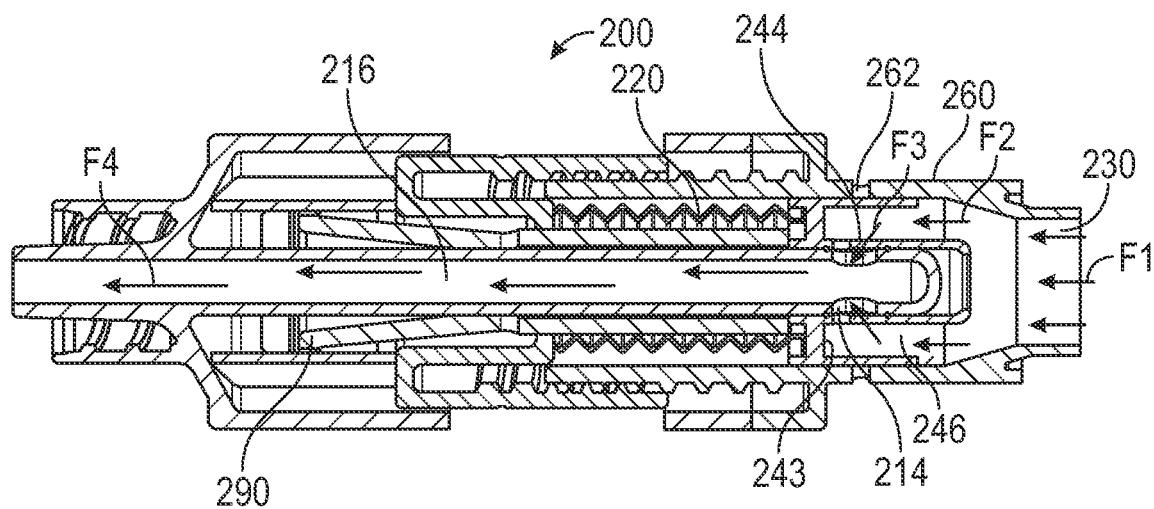
FIG. 19 depicts a cross-section front view of the needle-free connector assembly of FIG. 18 with full fluid flow, according to aspects of the disclosure.

Because the switch member 290 is in the regulation/indication mode, when the valve 240 slides downstream enough to show the red indicator band 242a through the viewing windows 262, the flow openings 214 of the plunger tip 212 are blocked by the inner wall 247 of the valve 240, thus blocking fluid in the valve channels 246 from entering the lumen 216 (see FIG. 17). Here, fluid flows into the inlet port 230 as indicated by fluid flow arrows F1 and through the valve channels 246 as indicated by fluid flow arrows F2, but is then blocked from proceeding further by the misalignment between the valve openings 244 and the flow openings 214 (e.g., the fluid flow F2 flows into the valve openings 244, but is then blocked by the exterior surface of the plunger tip 212, and the inner wall 247 blocks the fluid flow F2 from reaching the valve openings 244). Thus, in the dual regulation/indication mode, the needle-free connector 200 automatically shuts off fluid flow through the lumen 216 and to the outlet port 250 when the pressure exceeds the desired level.

For example, if the user pushes the syringe 195 too quickly, the increased fluid pressure moves the valve 240 downstream such that the red indicator band 242a is aligned with the viewing windows 262, giving an instant visual indicator to the user that the fluid pressure is exceeding the desired threshold (e.g., over 25 psi), and such that the flow openings 214 and the valve openings 244 are each blocked, thus automatically shutting off the fluid flow through the needle-free connector 200. At this point, the user can immediately ease off on pushing the fluid so that the fluid pressure eases and a biasing force of the bellows 220 causes the bellows 220 to expand. The expanding of the bellows 220 pushes the valve 240 back upstream until the green indicator band 242b is again aligned with the viewing windows 262 and the valve openings 244 are again aligned with the flow openings 214, thus allowing fluid to flow through the needle-free connector 200 again.

In use when the needle-free connector assembly 200 is in the pressure indication only mode (e.g., regulation off), as shown in FIGS. 18-21, the switch member 290 is set in the indication only position (e.g., upstream position) as shown by the outer surface 296 of the protrusion 294 within the switch window 276. Again, the sealing member 232 is removed and a fluid source (e.g., needle-free syringe, IV tube) is connected to the inlet port 230. Thus, fluid flows into the inlet port 230 as indicated by fluid flow arrows F1, through the valve channels 246 as indicated by fluid flow arrows F2, through the valve openings 244/flow openings 214 as indicated by fluid flow arrows F3 and through the lumen 216 to the outlet port 250 as indicated by fluid flow arrows F4 (see FIGS. 18 and 19). Here, the pressure due to the fluid flow acts on the pressure pad 243 of the valve 240, causing the valve 240 to slide linearly within the indicator housing 260. As the valve 240 moves within the indicator housing 260, different indicator bands 242 may in turn be aligned with the viewing windows 262 of the indicator housing 260, thus providing a view of the color of that indicator band 242 through the viewing windows 262.

Figure 20:
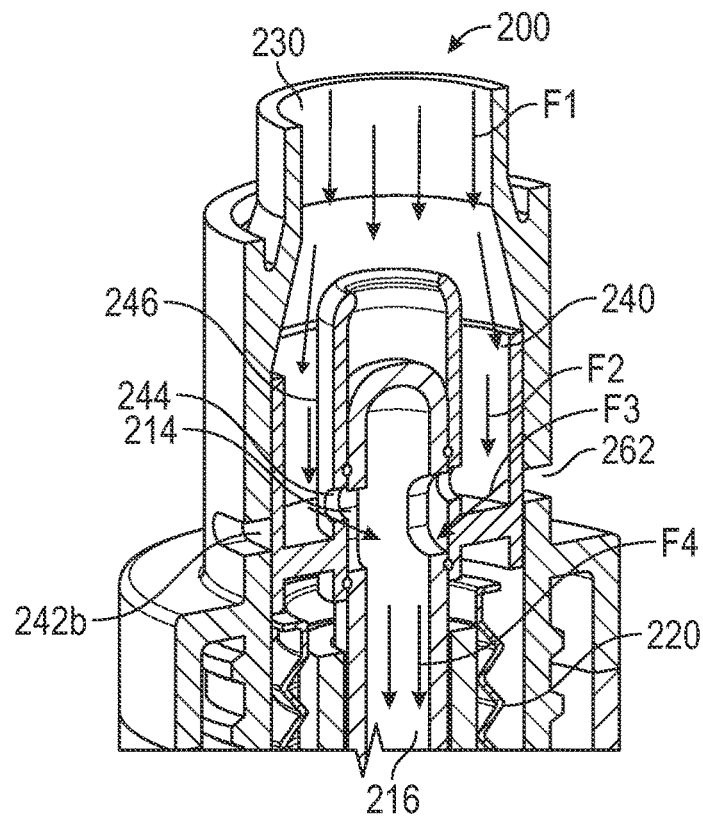
FIG. 20 depicts a cross-section partial perspective view of the needle-free connector assembly of FIG. 18 with desired fluid flow pressure, according to aspects of the disclosure.
Figure 21:
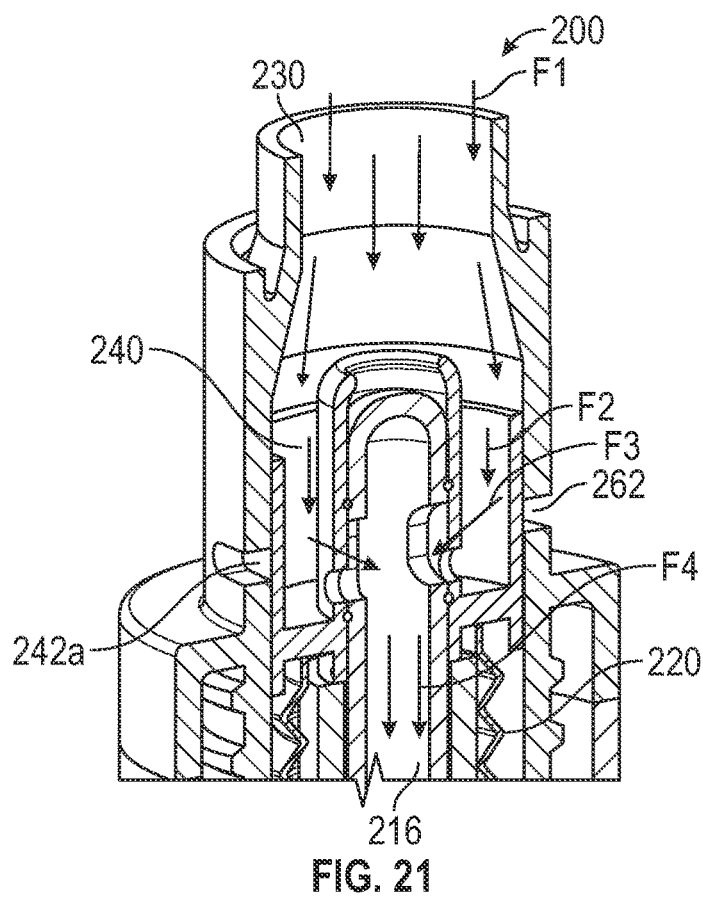
FIG. 21 depicts a cross-section partial perspective view of the needle-free connector assembly of FIG. 18 with excessive fluid flow pressure, according to aspects of the disclosure.

For example, in desired fluid pressure state of the needle-free connector 200, the green indicator band 242$b$ is aligned with the viewing windows 262 (as shown in FIG. 20) so that a user can easily and quickly see with a glance the green color in one or more of the viewing windows 262 and know that the fluid is currently flowing through the needle-free connector 200 at the desired pressure. As fluid is pushed into the needle-free connector 200 at higher pressure, such as by the user activating the needle-free syringe 195 shown in FIG. 4 or some other pressure inducing event, the bellows 220 compresses and the valve 240 slides downstream so that the red indicator band 242$a$ is aligned with the viewing windows 262 (as shown in FIG. 21), again providing a quick visual indication to the user through one or more of the viewing windows 262 that the fluid pressure is exceeding a desirable pressure range (e.g., 24-25 psi).

Because the switch member 290 is in the indication only mode, when the valve 240 slides downstream enough to show the red indicator band 242$a$ through the viewing windows 262, the stop surface 292 engages the downstream surface 241 of the valve 240 and prevents further downstream movement of the valve 240. Thus, the flow openings 214 of the plunger tip 212 do not become blocked by the inner wall 247 of the valve 240, and the valve channels 246 do not become blocked by an outer surface of the plunger tip 212. Thus, fluid continues to flow into the inlet port 230 as indicated by fluid flow arrows F1, through the valve channels 246 as indicated by fluid flow arrows F2, through the shifted valve openings 244/flow openings 214 (e.g., valve openings 244 shift from alignment with upstream portion of flow openings 214 to downstream portion of flow openings 214) as indicated by fluid flow arrows F3 and through the lumen 216 to the outlet port 250 as indicated by fluid flow arrows F4 (see FIG. 21).

For example, if the user pushes the syringe 195 too quickly, the increased fluid pressure moves the valve 240 downstream such that the red indicator band 242$a$ is aligned with the viewing windows 262, giving an instant visual indicator to the user that the fluid pressure is exceeding the desired threshold (e.g., over 25 psi). However, though the alignment of the valve openings 244 in relation to flow openings 214 shifts (e.g., from upstream to downstream portion of flow openings 214), the fluid flow continues through the needle-free connector 200. At this point, the user can still ease off on pushing the fluid so that the fluid pressure eases and a biasing force of the bellows 220 causes the bellows 220 to expand. The expanding of the bellows 220 pushes the valve 240 back upstream until the green indicator band 242$b$ is again aligned with the viewing windows 262 and the valve openings 244 are again aligned with the flow openings 214, thus indicating that the fluid is flowing through the needle-free connector 200 at the desired pressure again.

With regard to the needle-free connector 200, downstream force is exerted on the pressure pad 243 at the downstream end of the valve channels 246 due to the fluid pressure from the fluid flowing through the needle-free connector 200. The bellow 220 stiffness may be calculated where, for example, the surface area of the pressure pad 243 is 20 millimeters squared (mm$^2$), a desired fluid pressure is 25 psi and a pressure on the pressure pad 243 is 0.173 Newtons (N)/mm$^2$. Thus, the downward force necessary to move the valve 240 is the pressure 0.173 N/mm$^2$ times the surface area 20 mm$^2$, which equals 3.46 N.

Figure 22:
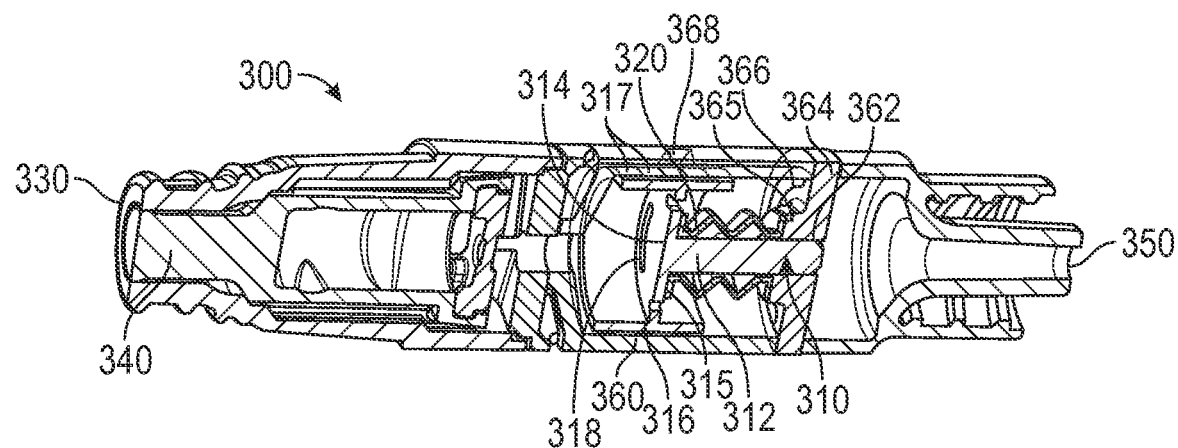
FIG. 22 depicts a cross-section perspective view of a needle-free connector assembly, according to aspects of the disclosure.
Figure 23:
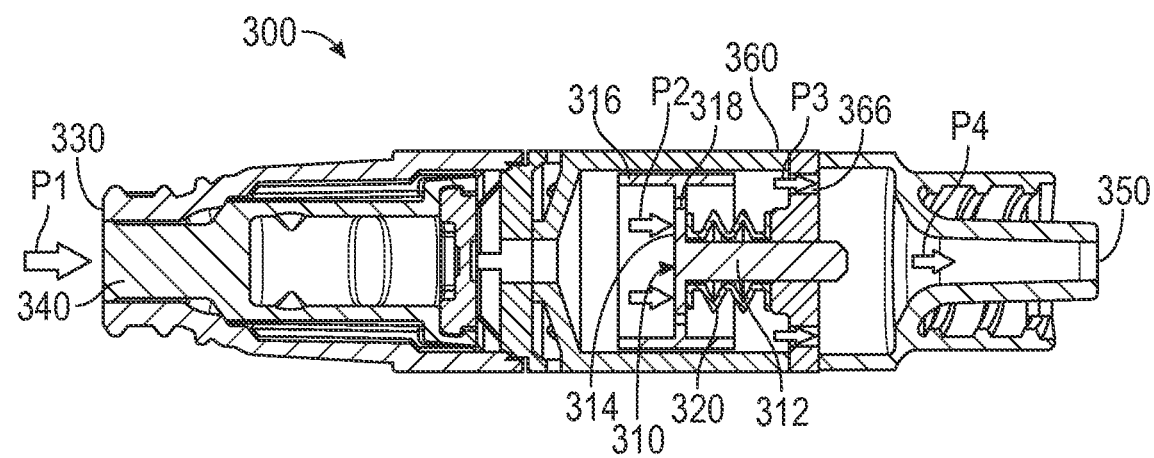
FIG. 23 depicts a cross-section front view of the needle-free connector assembly of FIG. 22 during use, according to aspects of the disclosure.

As shown in FIGS. 22 and 23, a needle-free connector assembly 300 is provided according to aspects of the disclosure. Needle-free connector 300 has a plunger 310 coupled to an elastomeric bellows 320, as well as an inlet port 330, a deformable valve 340 and an outlet port 350. The plunger 310 and bellows 320 are disposed within an indicator housing 360, where the plunger 310 includes a spindle 312 coupled to an end face 314, which in turn is coupled to a barrel 316 slidably disposed within the indicator housing 360. The end face 314 includes one or more flow openings 318 (e.g., arcuate slots) that allow fluid to flow through the end face 314.

The indicator housing 360 includes an end face 364 downstream of the end face 314 of the plunger 310, the end face 364 having a bore 362 that slidingly receives the spindle 312 and one or more flow openings 366 that allow fluid to flow through to the outlet port 350. The indicator housing 360 also includes a viewing window 368. The bellows 320 is disposed between and engaged by a downstream surface 315 of the end face 314 and an upstream surface 365 of the end face 364. The bellows 320 may be formed of a soft or pliable material that provides for repeated compression and expansion of the bellows 320. The material of the bellows 320 may be designed to provide a desired amount of biasing force to cause the bellows 320 to push in an opening or expanded direction. Thus, a specific amount of fluid flow pressure is required to overcome the biasing force and cause the bellows 320 to move in a closed or compressed direction.

The barrel 316 includes multiple indicator bands 317 disposed on the outer surface of the barrel 316. The indicator bands 317 may have visual differences (e.g., colors, shadings, textures, written words). For example, a furthermost upstream indicator band 317$a$ may be red to indicate the fluid pressure is higher than the desired threshold (e.g., 25 psi), the adjacent downstream indicator band 317$b$ may be green to indicate the fluid pressure is in the ideal range (e.g., just below 25 psi) and the furthermost downstream indicator band 317$c$ may be yellow to indicate the fluid pressure is nearly zero (e.g., little or no fluid flow).

In use, fluid flows into the inlet port 330 as indicated by fluid flow arrow P1, past the deformable valve 340 and into the indicator housing 360. Here, the majority of the fluid flow pushes up against the end face 314 as shown by fluid flow arrows P2, where the force of the fluid flow P2 against the end face 314 is transmitted to the bellows 320, which then compresses, causing the spindle 312 to slide linearly through the bore 362 and the barrel 316 to slide linearly within the indicator housing 360. As the barrel 316 moves within the indicator housing 360, different indicator bands 317 may in turn be aligned with the viewing window 368 of the indicator housing 360, thus providing a view of the color of that indicator band 317 through the viewing window 368. Some of the fluid flows through the flow openings 318 of the end face 314 and out the flow openings 366 of the end face 364 as shown by fluid flow arrows P3, and then out the outlet port 350 as shown by fluid flow arrow P4.

Figure 24A:
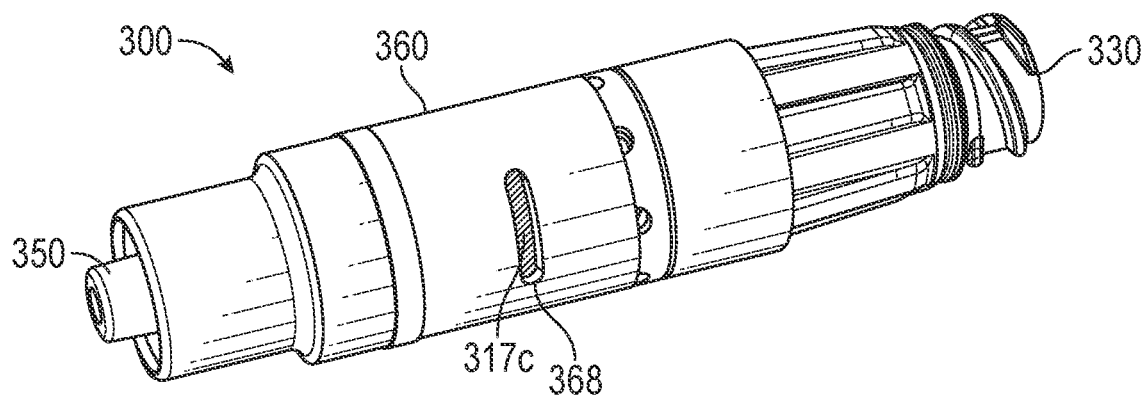
FIGS. 24A to 24C depict perspective views of the needle-free connector assembly of FIG. 22 at different flow pressures, according to aspects of the disclosure.
Figure 24B:
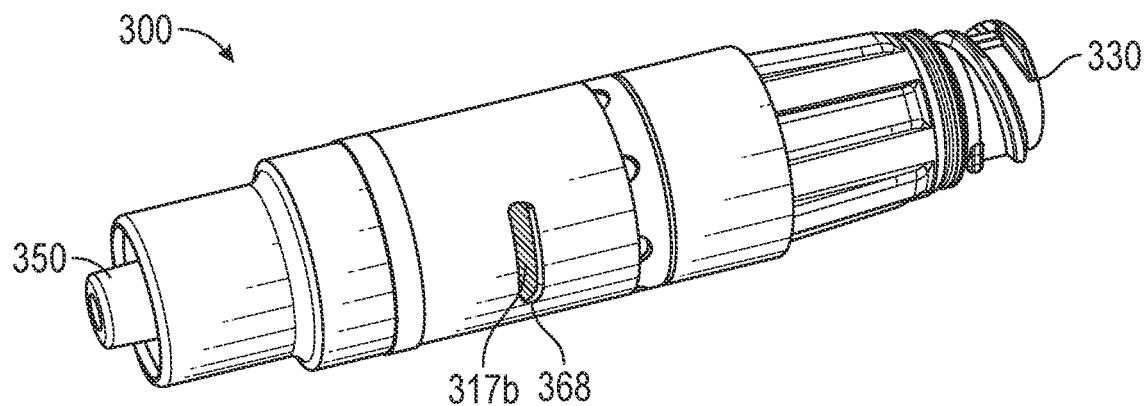

For example, in an initial state prior to fluid flow into the needle-free connector 300, the yellow indicator band 317c is aligned with the viewing window 368 (as shown by a first cross-hatching in FIG. 24A) so that a user can easily and quickly see with a glance the yellow color in the viewing window 368 and know that little or no fluid is currently flowing through the needle-free connector 300. As fluid is pushed into the needle-free connector 300, such as by the user activating the needle-free syringe 195 shown in FIG. 4, the bellows 320 compresses and the barrel 316 slides downstream so that the green indicator band 317b is aligned with the viewing window 368 (as shown by a second cross-hatching in FIG. 24B), again providing a quick visual indication to the user through the viewing window 368 that the fluid pressure is within a desirable pressure range (e.g., 24-25 psi).

Figure 24C:
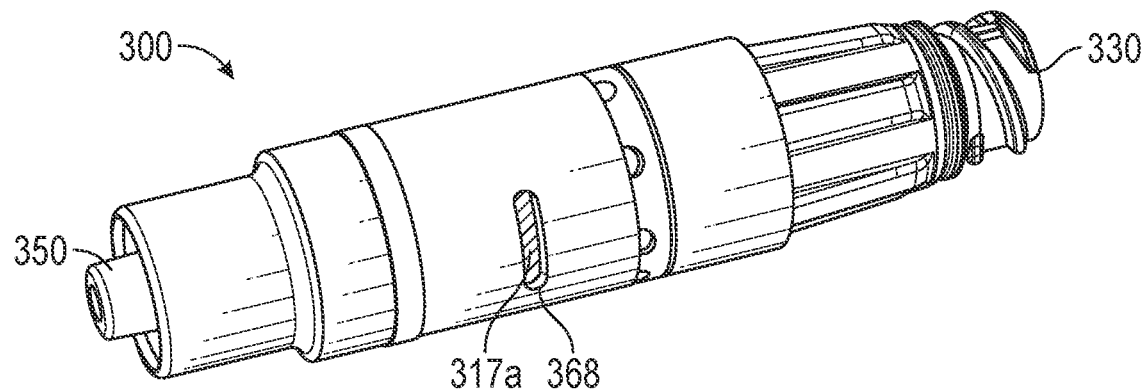

If the user pushes the syringe 195 too quickly, the increased fluid pressure moves the barrel 316 even further downstream such that the red indicator band 317a is now aligned with the viewing window 368 (as shown by a third cross-hatching in FIG. 24C), giving an instant visual indicator to the user that the fluid pressure is exceeding the desired threshold (e.g., over 25 psi). At this point, the user can immediately ease off on pushing the fluid so that the fluid pressure eases and a biasing force of the bellows 320 caused the bellows 320 to expand to push the barrel 316 back upstream until the green indicator band 317b is again aligned with the viewing window 368.

With regard to the needle-free connector 300, downstream force is exerted on the end face 314 of the plunger 310 due to the fluid pressure from the fluid flowing through the needle-free connector 300. The bellows 320 stiffness may be calculated where, for example, the surface area of the end face 314 is 42 millimeters squared ($mm^2$), a desired fluid pressure is 25 psi and a pressure on the end face 314 is 0.173 Newtons (N)/$mm^2$. Thus, the downward force necessary to move the plunger 310 is the pressure 0.173 N/$mm^2$ times the surface area 42 $mm^2$, which equals 7.266 N.

Figure 25:
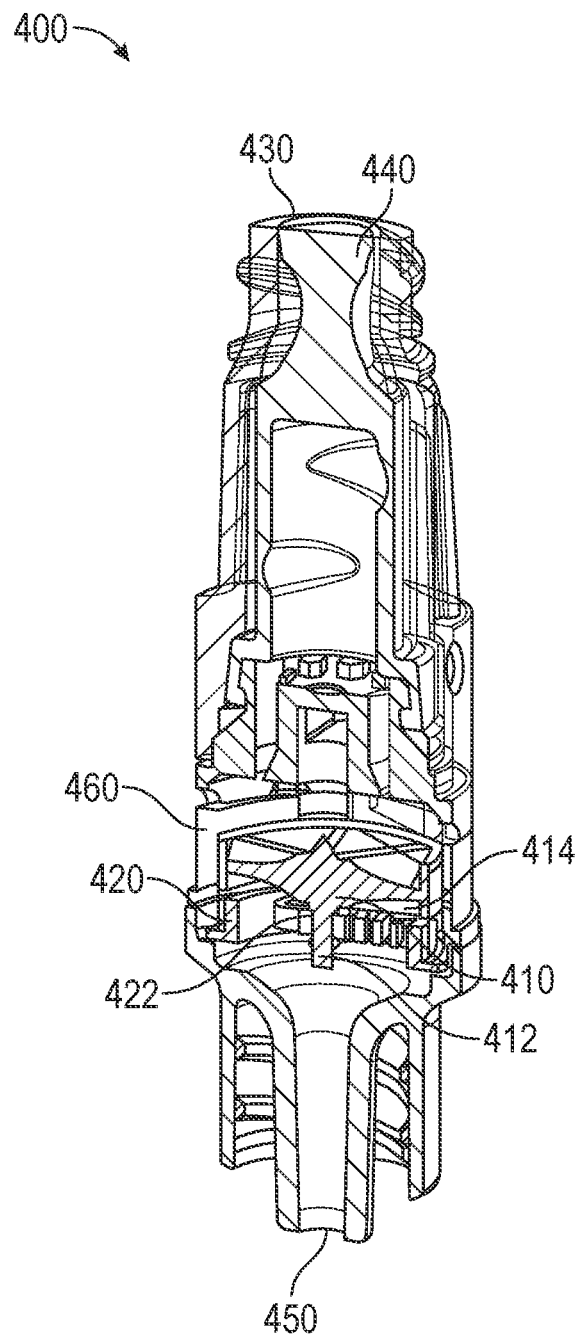
FIG. 25 depicts a cross-section perspective view of a needle-free connector assembly, according to aspects of the disclosure.
Figure 26:
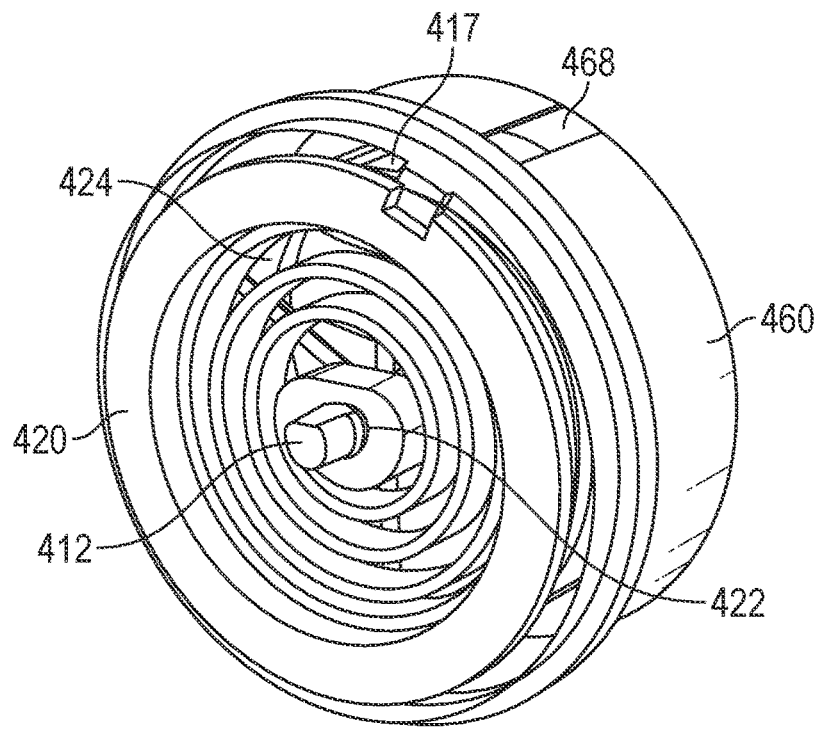
FIG. 26 depicts a perspective view of an indicator portion of the needle-free connector assembly of FIG. 25, according to aspects of the disclosure.
Figure 27:
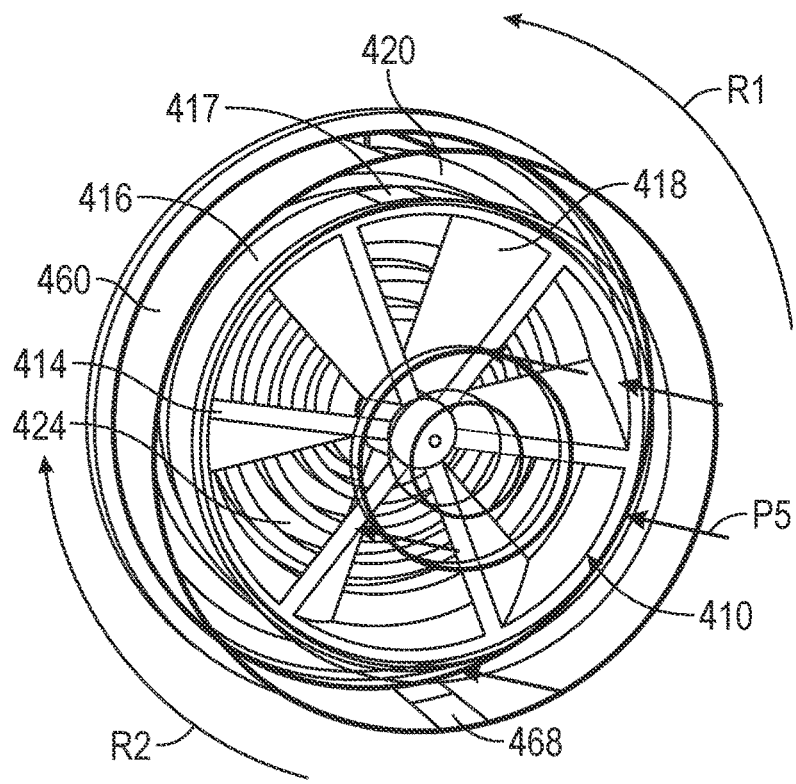
FIG. 27 depicts a perspective view of the indicator portion of FIG. 26 during use, according to aspects of the disclosure.

As shown in FIGS. 25-27, a needle-free connector assembly 400 is provided according to aspects of the disclosure. Needle-free connector 400 has a turbine 410 (e.g., Kaplan turbine) coupled to a spring 420 (e.g., torsional elastomer spring), as well as an inlet port 430, a deformable valve 440 and an outlet port 450. The turbine 410 and spring 420 are disposed within an indicator housing 460, where the turbine 410 includes a spindle 412 coupled to a bore 422 in the spring 420. The turbine 410 also includes multiple blades 414 that radiate outward from the spindle 412 and connect with a barrel 416 having an outer circumference, where the blades 414 are angled to present a flow face 418 to the linear fluid flow as shown by fluid flow arrows P5. The barrel 416 is rotationally disposed within the indicator housing 460, which has a viewing window 468.

The material of the spring 420 may be designed to provide a desired amount of biasing force to cause an uncompressed spring to stay in an open position or to cause a compressed spring 420 to rotate in an opening or expanded direction R1. Thus, a specific amount of fluid flow pressure is required to overcome the biasing force and cause the spring 420 to rotate in a closed or compressed direction R2.

The barrel 416 includes multiple indicator areas 417 disposed on the outer surface of the barrel 416. The indicator areas 417 may have visual differences (e.g., colors, shadings, textures, written words). For example, a first indicator area 417a may be red to indicate the fluid pressure is higher than the desired threshold (e.g., 25 psi), a second indicator area 417b may be green to indicate the fluid pressure is in the ideal range (e.g., just below 25 psi) and a third indicator area 417c may be yellow to indicate the fluid pressure is nearly zero (e.g., little or no fluid flow).

In use, fluid flows into the inlet port 430 and hits the angled blades 414 of the turbine 410, which generates axial and radial force on the turbine 410. The axial force is arrested within the indicator housing 460, while the radial force causes the blades 414 to twist according to the reactive force given by torsional elastomer spring 420, causing the turbine 410 to move rotationally within the indicator housing 460. As the barrel 416 moves within the indicator housing 460, different indicator areas 417 may in turn be aligned with the viewing window 468 of the indicator housing 460, thus providing a view of the color of that indicator area 417 through the viewing window 468. Some of the fluid flows through flow openings 424 of the spring 420 and out through the outlet port 450.

Figure 28A:
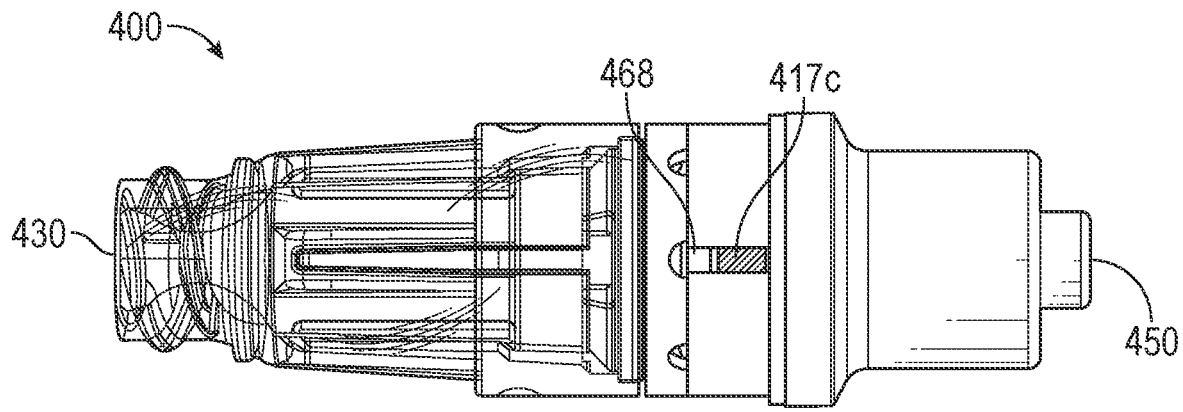
FIGS. 28A to 28C depict front views of the needle-free connector assembly of FIG. 25 at different flow pressures, according to aspects of the disclosure.
Figure 28B:
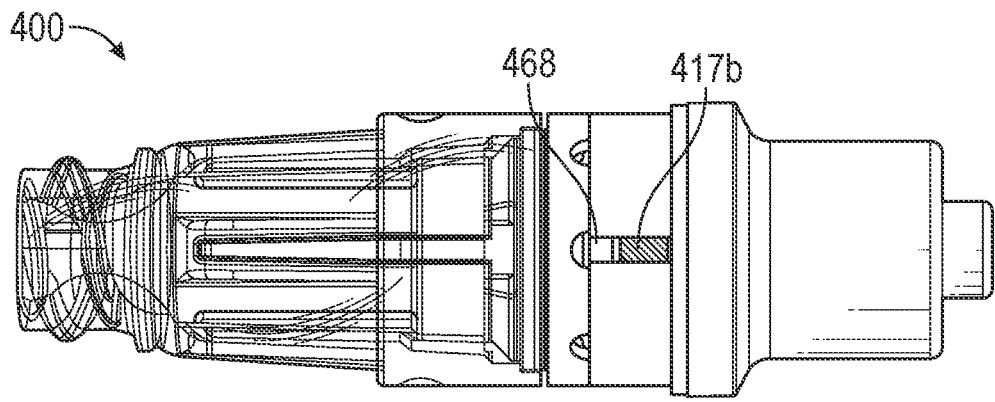

For example, in an initial state prior to fluid flow into the needle-free connector 400, the yellow indicator area 417c is aligned with the viewing window 468 (as shown by a first cross-hatching in FIG. 28A) so that a user can easily and quickly see with a glance the yellow color in the viewing window 468 and know that little or no fluid is currently flowing through the needle-free connector 400. As fluid is pushed into the needle-free connector 400, such as by the user activating the needle-free syringe 195 shown in FIG. 4, the blades 414 cause the turbine 410 to rotate and the barrel 416 rotates radially so that the green indicator area 417b is aligned with the viewing window 468 (as shown by a second cross-hatching in FIG. 28B), again providing a quick visual indication to the user through the viewing window 468 that the fluid pressure is within a desirable pressure range (e.g., 24-25 psi).

Figure 28C:
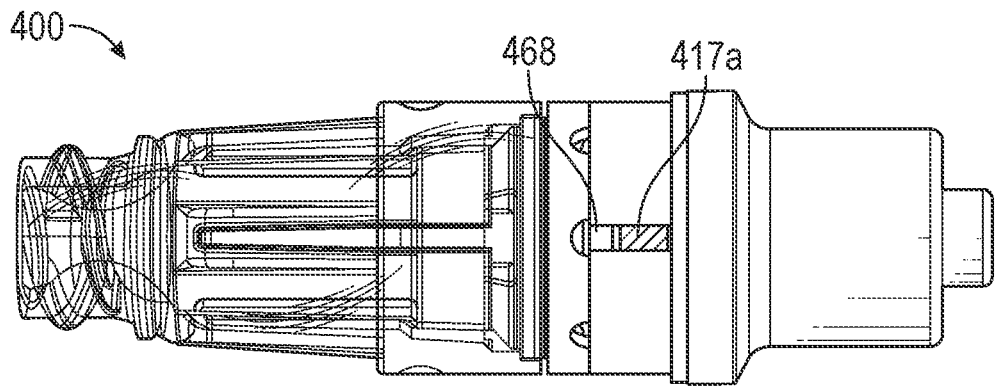

Again, if the user pushes the syringe 195 too quickly, the increased fluid pressure rotates the barrel 416 even further such that the red indicator area 417a is now aligned with the viewing window 468 (as shown by a third cross-hatching in FIG. 28C), giving an instant visual indicator to the user that the fluid pressure is exceeding the desired threshold (e.g., over 25 psi). At this point, the user can immediately ease off on pushing the fluid so that the fluid pressure eases and the biasing force of the spring 420 causes the turbine 410, and thus the barrel 416, to rotate back the opposite direction until the green indicator area 417b is again aligned with the viewing window 468.

The turning (e.g., rotation) of the turbine 410 may cause a swirling motion in the flow, thus creating turbulence in the fluid flow. The angle of the blades 414 may be designed to produce the desired amount of rotation of the turbine 410 for a target amount of fluid flow force or pressure, in combination with or based on the rotational stiffness (e.g., biasing force) of the spring 420.

Tables of force values are shown in FIG. 29 based on various sizes of syringes. For example, with a 3 milliliter (ml) syringe, a force on the plunger of the syringe (e.g., syringe 195) of 2.25 foot pounds (lbf) causes a fluid pressure of 25.08 psi, which is above the safety threshold of 25 psi. Similarly, a 5 ml syringe requires a 4.3 lbf force and a 10 ml syringe requires a 6.2 lbf force to exceed the safety threshold of 25 psi. Thus, it can be seen that for each size syringe there is a level of force that can be exerted by the user that causes the fluid pressure to exceed the desired maximum of 25 psi.

In aspects of the disclosure, the plunger 210, 310 and/or the turbine 410 may be formed of any suitable material. For example, the plunger 210, 310 and/or the turbine 410 may be formed from a hard material, such as polycarbonate, nylon, polyethylene, and the like. Similarly, the bellows 220, 320 and/or the spring 420 may be formed of any suitable material to provide the desired reactive or biasing force. For example, the bellows 220, 320 and/or the spring 420 may be formed from a springy material, such as silicone rubber, Nitrile rubber, ethylene propylene rubber, neoprene rubber and the like.

In aspects of the disclosure, the materials of the needle-free connectors 200, 300, 400 may be selected to allow for use of caustic fluids, such as chemotherapy drugs. In aspects of the disclosure, the bellows 220, 320 and/or the spring 420 may be stiffened to raise the fluid pressure ceiling (e.g., 30 psi), or softened to lower the fluid pressure ceiling (e.g., 20 psi). In aspects of the disclosure, visual indicators may be a series of lines and numbers similar to a tire gauge. For example, the valve 240 and the barrel 316, 416 may have a graphic showing a number of marking lines and corresponding pressures (e.g., 10 psi, 15 psi, 20 psi, etc.), such that as the bellows 220, 320 and/or the spring 420 expands or contracts, the current fluid pressure reading is centered in the viewing window 262, 368, 468.

In aspects of the disclosure, the visual indicators of the needle-free connector assembly 200, 300, 400 may be different colors, different patterns or any other visual display that quickly and effectively denotes different fluid pressures. In aspects of the disclosure, the needle-free connector assembly 200, 300, 400 may be used with a needle-based syringe. Here, for example, a sealing member (e.g., sealing member 232) may be left in place on the inlet port 230, 330, 430 and the needle of a syringe may be inserted through the sealing member 232 and into the inlet port 230, 330, 430.

In one or more embodiments of the disclosure, a needle-free connector assembly comprises a main housing; an indicator housing coupled to the main housing; a bellows disposed in the main housing; a plunger coupled to the bellows; an inlet port disposed at an upstream end of the indicator housing; an outlet port disposed at a downstream end of the main housing; a valve disposed within the indicator housing and adjacent the inlet port; and a switch member slidingly disposed in the main housing, wherein the needle-free connector assembly provides both flow regulation and pressure indication when the switch member is in a downstream position, and wherein the needle-free connector assembly provides only pressure indication when the switch member is in an upstream position.

In aspects of the disclosure, the plunger comprises a plunger tip that is slidingly received by a valve bore of the valve, the valve bore defined by an inner wall of the valve, and the plunger tip comprises a flow opening that fluidly couples an exterior of the plunger tip to a lumen defining a fluid flow path within the plunger. In aspects of the disclosure, the valve comprises a valve opening disposed on the inner wall of the valve, the valve opening coupled with a valve channel disposed within the valve, the valve channel fluidly coupled to the inlet port. In aspects of the disclosure, when the plunger tip is disposed within the valve bore such that the valve opening is at least partially aligned with the flow opening of the plunger tip, a fluid flow path is open from the valve channel, through the valve opening and through the flow opening into the lumen of the plunger. In aspects of the disclosure, when the plunger tip is disposed within the valve bore such that the valve opening is adjacent the inner wall, a fluid flow path from the valve channel is blocked by the inner wall and fluid is prevented from flowing into the flow openings and into the lumen.

In aspects of the disclosure, the indicator housing comprises a pressure viewing window extending through a wall of the indicator housing, wherein multiple indicator bands are disposed on an outer surface of the valve, each indicator band being viewable when aligned with the pressure viewing window. In aspects of the disclosure, a first pressure indicator band is positioned on the valve to indicate when viewed through the pressure viewing window that fluid pressure of fluid within the needle-free connector assembly is higher than a threshold fluid pressure, and wherein a second pressure indicator band is positioned downstream of the first indicator band to indicate when viewed through the pressure viewing window that the fluid pressure is within a desired range. In aspects of the disclosure, a third pressure indicator band is positioned downstream of the second indicator band to indicate when viewed through the pressure viewing window one of a fluid pressure below a desired range and no fluid pressure.

In aspects of the disclosure, an adjustment member is disposed within the main housing, the adjustment member comprising threads disposed on an inner surface of the adjustment member; and a downstream portion of the indicator housing is disposed within the main housing and comprising threads disposed on an outer surface of the downstream portion of the indicator housing, wherein the threads on the adjustment member are engaged with the threads disposed on the downstream portion of the indicator housing. In aspects of the disclosure, a pressure indicator band is disposed on an outer surface of the adjustment member, the pressure indicator band being viewable through an adjustment window disposed through a wall of the main housing. In aspects of the disclosure, the adjustment member is manipulable through the adjustment window to rotate the adjustment member to a preloaded pressure indicator setting.

In aspects of the disclosure, the bellows is compressed an amount based on the adjustment member setting, and wherein the bellows is biased towards an expanded position. In aspects of the disclosure, an upstream surface of the switch member comprises a stop surface configured to engage and prevent a downstream surface of the valve from moving further downstream within the indicator housing when the switch member is in the pressure indication only position. In aspects of the disclosure, the switch member comprises a protrusion sliding disposed within a switch window in the main housing, wherein the switch member flares outward from the plunger at a downstream end and is flexible at the downstream end.

In aspects of the disclosure, when the switch member is in the downstream position and the plunger is in a home position, flow openings of a tip of the plunger align with valve openings of the valve and a fluid flow pressure is less than or equal to a set pressure, and wherein when the switch member is in the downstream position and the plunger is in a regulation position, the flow openings of the plunger tip align with an inner wall of the valve so that fluid flow from valve channels of the valve is blocked and the fluid flow pressure is greater than the set pressure. In aspects of the disclosure, when the switch member is in the upstream position and the plunger is in a home position, an upstream portion of flow openings of a tip of the plunger align with valve openings of the valve and a fluid flow pressure is less than or equal to a set pressure, and wherein when the switch member is in the upstream position and the plunger is in a regulation position, a downstream portion of the flow openings of the plunger tip align with the valve openings of the valve and the fluid flow pressure is greater than the set pressure.

In one or more embodiments of the disclosure, a method of operating a needle-free connector in both a pressure regulation and pressure indication mode comprises: setting the switch member of the needle-free connector in the downstream position; rotating an adjustment member of the needle-free connector to a set pressure indicator setting; connecting a fluid source to the inlet port of the needle-free connector; flowing fluid from the fluid source into the inlet port, wherein pressure from the fluid flow causes the valve to slide within the indicator housing of the needle-free connector; viewing a first indicator on the valve through a viewing window of the needle-free connector when the fluid flow pressure is less than or equal to the set pressure, wherein the fluid flows through a valve channel and a valve opening of the valve, through a flow opening of a tip of the plunger into a lumen of the plunger and out the outlet port of the needle-free connector; and viewing a second indicator on the valve through the viewing window when the fluid flow pressure is greater than the set pressure, wherein the valve slides within the indicator housing so that the flow opening of the tip of the plunger is aligned with an inner wall of the valve and fluid flow from the valve channel is blocked.

In one or more embodiments of the disclosure, a method of operating a needle-free connector in pressure indication only mode comprises: setting the switch member of the needle-free connector in the upstream position; rotating an adjustment member of the needle-free connector to a set pressure indicator setting; connecting a fluid source to the inlet port of the needle-free connector; flowing fluid from the fluid source into the inlet port, wherein pressure from the fluid flow causes the valve to slide within the indicator housing of the needle-free connector; viewing a first indicator on the valve through a viewing window of the needle-free connector when the fluid flow pressure is less than or equal to the set pressure, wherein the fluid flows through a valve channel and a valve opening of the valve, through an upstream portion of a flow opening of a tip of the plunger into a lumen of the plunger and out the outlet port of the needle-free connector; and viewing a second indicator on the valve through the viewing window when the fluid flow pressure is greater than the set pressure, wherein the valve slides within the indicator housing until a stop member of the switch member engages a downstream surface of the valve, wherein the fluid flows through the valve channel and the valve opening of the valve, through a downstream portion of the flow opening of the tip of the plunger into the lumen of the plunger and out the outlet port of the needle-free connector.

In one or more embodiments of the disclosure, a needle-free connector assembly comprises: an indicator housing; an elastomeric bellows disposed in the indicator housing; a plunger disposed in the indicator housing and coupled to the elastomeric bellows, the plunger comprising: a barrel slidably disposed within the indicator housing; an end face coupled to the barrel, the end face having one or more flow openings configured to allow fluid to flow through the end face; and a spindle coupled to the end face; an inlet port disposed at an upstream end; an outlet port disposed at a downstream end; a deformable valve disposed adjacent the inlet port; and a viewing window disposed in the indicator housing, wherein a first indicator band disposed on an outer surface of the barrel is visible through the viewing window when the barrel is in a first position based on a fluid pressure being higher than a threshold pressure, and wherein a second indicator band disposed on the outer surface of the barrel is visible through the viewing window when the barrel is slid into a second position based on the fluid pressure being equal to or below the threshold pressure.

In one or more embodiments of the disclosure, a needle-free connector assembly comprises: an indicator housing; a spring disposed in the indicator housing; a turbine disposed in the indicator housing and coupled to the spring, the turbine comprising: a barrel rotationally disposed within the indicator housing; a spindle coupled to a bore in the spring; and a plurality of angled blades radiating outward from the spindle and coupled to the barrel; an inlet port disposed at an upstream end; an outlet port disposed at a downstream end; a deformable valve disposed adjacent the inlet port; and a viewing window disposed in the indicator housing, wherein a first indicator band disposed on an outer surface of the barrel is visible through the viewing window when the barrel is in a first position based on a fluid pressure being higher than a threshold pressure, and wherein a second indicator band disposed on the outer surface of the barrel is visible through the viewing window when the barrel is rotated into a second position based on the fluid pressure being equal to or below the threshold pressure.

In one or more embodiments of the disclosure, an infusion set comprises one or more infusion tubes; one or more infusion components coupled to the one or more infusion tubes; and a needle-free connector assembly. The needle-free connector assembly comprises a main housing; an indicator housing coupled to the main housing; a bellows disposed in the main housing; a plunger coupled to the bellows; an inlet port disposed at an upstream end of the indicator housing; an outlet port disposed at a downstream end of the main housing; a valve disposed within the indicator housing and adjacent the inlet port; and a switch member slidingly disposed in the main housing, wherein the needle-free connector assembly provides both flow regulation and pressure indication when the switch member is in a downstream position, and wherein the needle-free connector assembly provides only pressure indication when the switch member is in an upstream position.

In aspects of the disclosure, the inlet port is configured to receive one of a needle-free syringe and one of the one or more infusion tubes.

In one or more embodiments of the disclosure, a method of operating a needle-free connector in both a pressure regulation and pressure indication mode comprises: setting a switch member of the needle-free connector in a downstream position; rotating an adjustment member of the needle-free connector to a set pressure indicator setting; connecting a fluid source to an inlet port of the needle-free connector; flowing fluid from the fluid source into the inlet port, wherein pressure from the fluid flow causes a valve to slide within an indicator housing of the needle-free connector; viewing a first indicator on the valve through a viewing window of the needle-free connector when the fluid flow pressure is less than or equal to the set pressure, wherein the fluid flows through a valve channel and a valve opening of the valve, through a flow opening of a tip of a plunger into a lumen of the plunger and out an outlet port of the needle-free connector; and viewing a second indicator on the valve through the viewing window when the fluid flow pressure is greater than the set pressure, wherein the valve slides within the indicator housing so that the flow opening of the tip of the plunger is aligned with an inner wall of the valve and fluid flow from the valve channel is blocked.

In one or more embodiments of the disclosure, a method of operating a needle-free connector in a pressure indication only mode comprises: setting a switch member of the needle-free connector in an upstream position; rotating an adjustment member of the needle-free connector to a set pressure indicator setting; connecting a fluid source to an inlet port of the needle-free connector; flowing fluid from the fluid source into the inlet port, wherein pressure from the fluid flow causes a valve to slide within an indicator housing of the needle-free connector; viewing a first indicator on the valve through a viewing window of the needle-free connector when the fluid flow pressure is less than or equal to the set pressure, wherein the fluid flows through a valve channel and a valve opening of the valve, through an upstream portion of a flow opening of a tip of a plunger into a lumen of the plunger and out an outlet port of the needle-free connector; and viewing a second indicator on the valve through the viewing window when the fluid flow pressure is greater than the set pressure, wherein the valve slides within the indicator housing until a stop member of the switch member engages a downstream surface of the valve, wherein the fluid flows through the valve channel and the valve opening of the valve, through a downstream portion of the flow opening of the tip of the plunger into a lumen of the plunger and out the outlet port of the needle-free connector.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, inserting and the like via a hardware element.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needle-free connector assembly comprising:
   a main housing;
   an indicator housing coupled to the main housing;
   a bellows disposed in the main housing;
   a plunger coupled to the bellows;
   an inlet port disposed at an upstream end of the indicator housing;
   an outlet port disposed at a downstream end of the main housing;
   a valve disposed within the indicator housing and adjacent the inlet port; and
   a switch member slidingly disposed in the main housing,
   wherein the needle-free connector assembly provides both flow regulation and pressure indication when the switch member is in a downstream position, and wherein the needle-free connector assembly provides only pressure indication when the switch member is in an upstream position.

2. The needle-free connector assembly of claim 1, wherein the plunger comprises a plunger tip that is slidingly received by a valve bore of the valve, the valve bore defined by an inner wall of the valve, and wherein the plunger tip comprises a flow opening that fluidly couples an exterior of the plunger tip to a lumen defining a fluid flow path within the plunger.

3. The needle-free connector assembly of claim 2, wherein the valve comprises a valve opening disposed on the inner wall of the valve, the valve opening coupled with a valve channel disposed within the valve, the valve channel fluidly coupled to the inlet port.

4. The needle-free connector assembly of claim 3, wherein when the plunger tip is disposed within the valve bore such that the valve opening is at least partially aligned with the flow opening of the plunger tip, a fluid flow path is open from the valve channel, through the valve opening and through the flow opening into the lumen of the plunger.

5. The needle-free connector assembly of claim 3, wherein when the plunger tip is disposed within the valve bore such that the valve opening is adjacent the inner wall, a fluid flow path from the valve channel is blocked by the inner wall and fluid is prevented from flowing into the flow openings and into the lumen.

6. The needle-free connector assembly of claim 1, wherein the indicator housing comprises a pressure viewing window extending through a wall of the indicator housing, wherein multiple indicator bands are disposed on an outer surface of the valve, each indicator band being viewable when aligned with the pressure viewing window.

7. The needle-free connector assembly of claim 6, wherein a first pressure indicator band is positioned on the valve to indicate when viewed through the pressure viewing window that fluid pressure of fluid within the needle-free connector assembly is higher than a threshold fluid pressure, and wherein a second pressure indicator band is positioned downstream of the first indicator band to indicate when viewed through the pressure viewing window that the fluid pressure is within a desired range.

8. The needle-free connector assembly of claim 1, further comprising:
   an adjustment member disposed within the main housing, the adjustment member comprising threads disposed on an inner surface of the adjustment member; and
   a downstream portion of the indicator housing disposed within the main housing and comprising threads disposed on an outer surface of the downstream portion of the indicator housing,
   wherein the threads on the adjustment member are engaged with the threads disposed on the downstream portion of the indicator housing.

9. The needle-free connector assembly of claim 8, further comprising a pressure indicator band disposed on an outer surface of the adjustment member, the pressure indicator band being viewable through an adjustment window disposed through a wall of the main housing.

10. The needle-free connector assembly of claim 9, wherein the adjustment member is manipulable through the adjustment window to rotate the adjustment member to a preloaded pressure indicator setting.

11. The needle-free connector assembly of claim 10, wherein the bellows is compressed an amount based on the adjustment member setting, and wherein the bellows is biased towards an expanded position.

12. The needle-free connector assembly of claim 1, wherein an upstream surface of the switch member comprises a stop surface configured to engage and prevent a downstream surface of the valve from moving further downstream within the indicator housing when the switch member is in the pressure indication only position.

13. The needle-free connector assembly of claim 1, wherein the switch member comprises a protrusion sliding disposed within a switch window in the main housing, wherein the switch member flares outward from the plunger at a downstream end and is flexible at the downstream end.

14. The needle-free connector assembly of claim 13, wherein when the switch member is in the downstream position and the plunger is in a home position, flow openings of a tip of the plunger align with valve openings of the valve and a fluid flow pressure is less than or equal to a set pressure, and wherein when the switch member is in the downstream position and the plunger is in a regulation position, the flow openings of the plunger tip align with an inner wall of the valve so that fluid flow from valve channels of the valve is blocked and the fluid flow pressure is greater than the set pressure.

15. The needle-free connector assembly of claim 13, wherein when the switch member is in the upstream position and the plunger is in a home position, an upstream portion of flow openings of a tip of the plunger align with valve openings of the valve and a fluid flow pressure is less than or equal to a set pressure, and wherein when the switch member is in the upstream position and the plunger is in a regulation position, a downstream portion of the flow openings of the plunger tip align with the valve openings of the valve and the fluid flow pressure is greater than the set pressure.

16. A method of operating the needle-free connector of claim 1 in both a pressure regulation and pressure indication mode, the method comprising:
    setting the switch member of the needle-free connector in the downstream position;
    rotating an adjustment member of the needle-free connector to a set pressure indicator setting;
    connecting a fluid source to the inlet port of the needle-free connector;
    flowing fluid from the fluid source into the inlet port, wherein pressure from the fluid flow causes the valve to slide within the indicator housing of the needle-free connector;
    viewing a first indicator on the valve through a viewing window of the needle-free connector when the fluid flow pressure is less than or equal to the set pressure, wherein the fluid flows through a valve channel and a valve opening of the valve, through a flow opening of a tip of the plunger into a lumen of the plunger and out the outlet port of the needle-free connector; and
    viewing a second indicator on the valve through the viewing window when the fluid flow pressure is greater than the set pressure, wherein the valve slides within the indicator housing so that the flow opening of the tip of the plunger is aligned with an inner wall of the valve and fluid flow from the valve channel is blocked.

17. A method of operating the needle-free connector of claim 1 in a pressure indication only mode, the method comprising:
    setting the switch member of the needle-free connector in the upstream position;
    rotating an adjustment member of the needle-free connector to a set pressure indicator setting;
    connecting a fluid source to the inlet port of the needle-free connector;
    flowing fluid from the fluid source into the inlet port, wherein pressure from the fluid flow causes the valve to slide within the indicator housing of the needle-free connector;
    viewing a first indicator on the valve through a viewing window of the needle-free connector when the fluid flow pressure is less than or equal to the set pressure, wherein the fluid flows through a valve channel and a valve opening of the valve, through an upstream portion of a flow opening of a tip of the plunger into a lumen of the plunger and out the outlet port of the needle-free connector; and
    viewing a second indicator on the valve through the viewing window when the fluid flow pressure is greater than the set pressure, wherein the valve slides within the indicator housing until a stop member of the switch member engages a downstream surface of the valve, wherein the fluid flows through the valve channel and the valve opening of the valve, through a downstream portion of the flow opening of the tip of the plunger into the lumen of the plunger and out the outlet port of the needle-free connector.

* * * * *